United States Patent
Rogan et al.

(10) Patent No.: US 7,833,713 B2
(45) Date of Patent: Nov. 16, 2010

(54) MITIGATION OF COT-1 DNA DISTORTION IN NUCLEIC ACID HYBRIDIZATION

(75) Inventors: Peter K. Rogan, Overland Park, KS (US); Joan Knoll, Overland Park, KS (US); Heather Newkirk, Kansas City, MO (US)

(73) Assignee: The Children's Mercy Hospital, Kansas City, MO (US)

( * ) Notice: Subject to any disclaimer, the term of this patent is extended or adjusted under 35 U.S.C. 154(b) by 184 days.

(21) Appl. No.: 11/561,004

(22) Filed: Nov. 17, 2006
(Under 37 CFR 1.47)

(65) Prior Publication Data

US 2008/0050728 A1 Feb. 28, 2008

Related U.S. Application Data

(60) Provisional application No. 60/737,986, filed on Nov. 18, 2005.

(51) Int. Cl.
*C12Q 1/68* (2006.01)
*C12P 19/34* (2006.01)

(52) U.S. Cl. .......................................... 435/6; 435/91.1

(58) Field of Classification Search ........................ None
See application file for complete search history.

(56) References Cited

U.S. PATENT DOCUMENTS

| 5,447,841 | A | 9/1995 | Gray |
| 5,721,098 | A | 2/1998 | Pinkel et al. |
| 6,013,440 | A * | 1/2000 | Lipshutz et al. ............... 506/7 |
| 6,268,147 | B1 | 7/2001 | Beattie |
| 6,828,097 | B1 * | 12/2004 | Knoll et al. .................. 435/6 |
| 6,962,778 | B1 | 11/2005 | Coull et al. |

FOREIGN PATENT DOCUMENTS

| WO | 9824933 | 6/1998 |
| WO | WO0188089 A2 | 11/2001 |
| WO | 03020902 | 3/2003 |
| WO | 03027328 | 4/2003 |
| WO | 2004050910 | 6/2004 |

OTHER PUBLICATIONS

Craig et al. Removal of repetitive sequences from FISH probes using PCR-assisted affinity chromatography. Hum. Genet., Sep. 1997, vol. 100, No. 3-4, pp. 472-476.
Dugan et al. Polymerase chain reaction based suppression of repetitive sequences in whole chromosome painting probes for FISH. Chromosome Res. 2003, vol. 3, pp. 27-32.
Chung, et al., The use of cloned repetitive sequences as hybridization competitors to detect single copy sequences., Genetic Analysis: Biomolecular Eng., 1997, vol. 14 pp. 13-15.
Pinkel, et al., High resolution analysis of DNA copy number variation using comparative genomic hybridization to microarrays., Nature America Inc., http;//genetics.nature.com, Oct. 20, 1998, vol. 20 pp. 207-211.
Newkirk, et al., Distortion of quantitative genomic and expression hybridization by Cot-1 DNA; mitigation of this effect., Nucleic Acids Research., 2005, vol. 33. No. 22, e191.
Hizume, et al., Cloning of DNA sequences localized on proximal fluorescent chromosome bands by microdissection in *Pinus densiflora* Sieb. & Zucc., Chromosoma., 2001, vol. 110, pp. 345-351.
Mrazek, et al., UNIREP: A microcomputer program to find unique and repetitive nucleotide sequences in genomes., Cabios., 1993, vol. 9. No. 3, pp. 355-360.
Horng, et al., Database of Repetitive Elements in Complete Genomes and Data Mining Using Transcription Factor Binding Sites., Ieee Transactions on Information Technology in Biomedicine., Jun. 2003., vol. 7. No. 2., pp. 93-100.

* cited by examiner

*Primary Examiner*—Kenneth R. Horlick
*Assistant Examiner*—David C Thomas
(74) *Attorney, Agent, or Firm*—Polsinelli Shughart PC; Tracey S. Truitt

(57) ABSTRACT

A novel method of suppressing non-specific cross-hybridization between repetitive elements present in nucleic acid probes and corresponding repetitive elements in the target nucleic acid by using DNA synthesized to contain a plurality of repetitive elements while avoiding low and single copy sequences.

14 Claims, 4 Drawing Sheets

Fig. 3

| Potential Structures | Description | Probes | Reactions |
|---|---|---|---|
| 1. | Expected hybridization of microsphere conjugated probe to target sc sequence | HOXB1 | Table 1: 7-12, 32, 33 |
| 2. | Hybridization of probe to C₀t-1 sc sequence | ABL1a, ABL1b, RRP41.6a, ABL1AluMER1, DNJA3Alu | Table 1: 2, 14, 18, 20, 22, 30, 31<br>Table 3: 2, 3, 5, 6, 8, 9, 11, 12, 14, 16, 18 |
| 3. | Hybridization of probe to sc sequence in C₀t-1 DNA with subsequent hybridization to repeat-containing C₀t-1 fragment | ABL1a, ABL1AluMER1, C1QTNF7 | Table 1: 14, 20, 22, 24, 25, 27, 28, 31<br>Table 3: 2, 3, 14, 16 |
| 4. | Hybridization of probe to sc sequence in labeled target pre-hybridized to unlinked C₀t-1-derived repetitive sequence | PMP22, TEKT3, ABL1a, ABL1b, ABL1AluMER1 | Table 1: 2, 4, 6, 14, 16-18, 20, 22, 31<br>Table 3: 14, 16, 18 |

Legend:
- ———— Single copy (sc) sequence in C₀t-1 DNA
- ———·-· Repetitive sequence flanking sc sequence in C₀t-1 DNA
- ———— Sc sequence in target DNA
- ———·-· Sc sequence in target DNA flanking a repetitive element
- ●———— Microsphere-conjugated sc probe

MITIGATION OF COT-1 DNA DISTORTION IN NUCLEIC ACID HYBRIDIZATION

CROSS REFERENCE TO RELATED APPLICATION

This application claims the benefit of the prior filed, co-pending provisional application Ser. No. 60/737,986, filed Nov. 18, 2005, which is hereby incorporated by reference.

SEQUENCE LISTING

A printed Sequence Listing, hereby incorporated by reference, accompanies this application, and has also been submitted with identical contents in the form of a computer-readable ASCII file in the electronic filing system of the U.S.P.T.O.

BACKGROUND OF THE INVENTION

1. Field of the Invention

The present invention concerns materials and methods for suppressing non-specific cross-hybridization between repetitive elements present in the target genome or transcriptome and corresponding repetitive elements in nucleic acid probes, while avoiding incidental hybridization between single copy sequences in the probes and adventitious single copy sequences in suppression DNA. More particularly, the present invention concerns the development and use of probes substantially lacking repetitive sequences along with the development and use of suppressive, synthetic repetitive DNA substantially devoid of single copy elements. Even more particularly, such repetitive DNA comprises repetitive sequences corresponding to moderate to high copy repetitive elements adjacent to single copy elements in one or more representative genomic regions.

2. Description of the Prior Art

Genome-wide analysis of gene expression and locus copy number has been facilitated by microarray and array-based comparative genomic hybridization. Persistent questions regarding reproducibility of these techniques have been raised by cross-validation studies in different laboratories[1-5]. Strategies to mitigate variability in the results obtained from replicate studies have focused on standardizing technical factors, such as array production, RNA synthesis, labeling, hybridization, scanning, and data analysis[6-8]. Zakharkin et al[9] suggest that biological differences among samples is the largest source of this variability and these other factors contribute to a lesser degree.

When analyzing DNA using a hybridization probe, repetitive sequences in the target DNA typically must be blocked prior to hybridization of the probe to the target, in order to avoid high background hybridizations between repetitive elements in the probe and homologous repetitive elements in the target.

Repetitive sequences occur in multiple copies in the haploid genome. The number of copies can range from two to hundreds of thousands, wherein the Alu family of repetitive DNA are exemplary of the latter numerous variety. The copies of a repeat may be clustered or interspersed throughout the genome. Repeats may be clustered in one or more locations in the genome, for example, repetitive sequences occurring near the centromeres of each chromosome, and variable number tandem repeats (VNTRs) Nakamura et al, Science, 235: 1616 (1987); or the repeats may be distributed by Bardoni et al., Cytogenet. Cell Genet., 46: 575 (1987); or the repeats may be distributed over all the chromosomes, for example, the Alu family of repetitive sequences.

Simple repeats of low complexity can be found within genes but are more commonly found in non-coding genomic sequences. Such repeated elements consist of mono-, di-, tri-, tetra-, or penta-nucleotide core sequence elements arrayed in tandem units. Often the number of tandem units comprising these repeated sequences varies at the identical locations among genomes from different individuals. These repetitive elements can be found by searching for consecutive runs of the core sequence elements in genomic sequences.

Competition hybridization, also known as suppression hybridization, provides a means for blocking a potentially overwhelming repetitive DNA signal. The unlabeled competitor or suppressor DNA contains high incidents of repetitive elements which bind to homologous repetitive elements in the target, thereby preventing repetitive portions of the labeled probes from binding to such repetitive elements in the target and increasing the likelihood that the probes will hybridize substantially to the targeted, typically non-repetitive, sequence.

The use of repetitive sequence-enriched ($C_o t$-1) DNA to suppress or block non-specific cross hybridization between repetitive elements present in the probe with other locations in the genome (or transcriptome) is a common requirement for most microarray hybridization studies. Hybridization of suppressor DNA such as $C_o t$-1 to target DNA prior to FISH is commonly practiced in the prior art to avoid background, i.e. non-specific, hybridization. In humans, the $C_o t$-1 fraction is highly concentrated in families of interspersed repetitive elements, such as short and long interspersed repetitive elements, SINEs and LINEs[10, 11]. Commercial procedures for $C_o t$-1 DNA preparation iterate denaturation and re-annealing of genomic DNA, and are monitored by enrichment for Alu elements (three-fold excess over the corresponding level in the normal genome) and L1 elements (four-fold excess over the corresponding level in the normal genome). Current quality control procedures do not determine the precise composition or sequence of $C_o t$-1 DNA.

While the $C_o t$-1 fraction appears to suppress non-specific hybridization between the repetitive elements of the probe and corresponding or homologous repetitive elements of the target DNA, it also increases experimental noise[12] (FIG. 1). Therefore, it was investigated whether differences in $C_o t$-1 composition could be a major source of variability in results from genomic hybridization studies. The role of $C_o t$-1 in genomic hybridization was elucidated by quantitative microsphere by hybridization (QMH)[13,20] using sequence-defined, genomic single copy (sc) probes[14] and probes composed of contiguous sc and repetitive genomic sequences. It was determined that $C_o t$-1 promotes the formation of stable duplexes (single copy sequences in the probe sequence hybridized to the single copy sequences within the Cot-1 DNA) containing adjacent paralogous repetitive sequences often unrelated to the probe, thereby preventing accurate quantification of single copy sequence hybridization. Incidents of single copy elements within the $C_o t$-1 hybridized to homologous single copy elements in the probe, distort (falsely amplify) the probe signal.

FIG. 1 illustrates hybridization of $C_o t$-1 105 to a genomic DNA target 100 to suppress or block a repetitive element 115 in the target 100 from being available for hybridization with paralogous repetitive elements 120 in the probes 110. Repetitive element 115 is shown in parallel relation to the suppressing repetitive element 117 in the $C_o t$-1 DNA 105, thereby indicating hybridization of the elements 115 to 117. As is typical in the prior art, probes 100 include both single copy elements 135 as well as adventitious repetitive elements 120, the single copy elements 135 being selected and synthesized to selectively hybridize to homologous single copy elements 140 in the target 100. As illustrated, the probes 110 are conjugated to microspheres 145 used for probe 110 detection and quantitation. Probe 110' is shown hybridized to the target 100, as anticipated by the study design. In addition to hybridizing to the repetitive element in the target 115, however, single copy elements 130 in the $C_o$t-1 105 also hybridize to homologous single copy elements 135 in the probe 125, thereby increasing the probe signal by three fold.

Patent application PCT/US2006/032693 entitled "Quantification of Microsphere Suspension Hybridization and Uses Thereof", filed Aug. 16, 2006, describes a microsphere suspension hybridization assay utilizing low or single copy genomic hybridization probes allowing direct analysis of whole genomic DNA or RNA) using flow cytometry and is hereby incorporated by reference.

Accordingly, what is needed in the art are methods of suppressing signal distortion caused by hybridization of nucleic acid probes to elements present in $C_o$t-1 DNA, methods of suppressing non-specific hybridization of probes to target DNA; methods of suppressing hybridization of suppressing or competitive DNA to single copy sequences in the target as well as in the probes; methods of identifying and synthesizing suppressive, repetitive DNA; synthesized, repetitive DNA products efficacious for use as suppressor DNA; and nucleic acid hybridization systems utilizing such synthesized suppressive DNA in combination with single copy probes substantially devoid of repetitive elements.

SUMMARY OF THE INVENTION

The present invention overcomes the problems outlined above and provides novel methods and products for suppressing the result-distorting effect of $C_o$t-1 DNA through replacement of $C_o$t-1 with suppressive nucleic acids synthesized to be rich in repeat elements but substantially devoid of single or low copy elements. Generally speaking, the method of the present invention includes the steps of preparing synthetic suppression DNA, and hybridizing the suppression DNA to target genomic DNA in order to block repetitive sequences in the target prior to hybridizing a probe with the target. Preferably, the probe will be free or substantially free of repetitive elements and the suppression DNA will be free or substantially free of single or low copy DNA stretches. In some preferred forms, the method will include the steps of preparing a hybridization probe by coupling a spectrally-encoded, polystyrene microsphere to a selected, low copy, synthetic DNA sequence; pre-hybridizing target genomic DNA with synthetic, suppressive or blocking DNA of the present invention; hybridizing the probe to the target genomic DNA, and detecting the product of the hybridization by flow cytometry. The demonstrated signal distortion caused by $C_o$t-1 in hybridization assays was thereby mitigated by suppressing cross-hybridization through pre-hybridization of the target to synthetic repetitive elements that are free or substantially free of single copy sequences, and preferably free or substantially free of low copy sequences.

Unlike current hybridization assays, an assay in accordance with the present invention substitutes $C_o$t-1 suppressive DNA with synthetic DNA developed to include selected repetitive elements without including competing single (or low) copy elements. Preferably, the synthetic DNA of the present invention is selected due to its homology with repetitive regions of target DNA flanking the single (or low) copy sequence of interest, which corresponds to, or is homologous with, the sequence of the single (or low) copy hybridization probe, which is designed to hybridize with the single (or low) copy sequence of interest.

The methods and products of the present invention are efficacious for mitigation of adventitious cross-hybridization (1) between repetitive elements in suppression DNA and homologous elements in probes, (2) between single or low copy elements in probes and homologous single (or low) copy elements in suppression DNA, and (3) between repetitive elements in the probe and homologous elements in target genomic sequences. Preferably, in accordance with the present invention, single or low copy probes are substantially, even more preferably, completely, devoid or repetitive elements, and suppression DNA is synthesized to be substantially, even more preferably, completely, devoid of single or low copy elements.

FIG. 2 illustrates hybridization of synthetic, suppressive DNA 205 to a genomic DNA target 200 to suppress or block a repetitive element 215 in the target. As shown, the synthetic, suppressive DNA 205 does not present adventitious single or low copy elements that would hybridize with single or low copy elements 235 in the probe 210 or single or low copy elements 240 in the target 200, thereby significantly reducing cross-hybridization of single or low copy elements in the assay. The probe 210 is preferably synthesized to comprise one or more single or low copy elements 235 but is devoid of repetitive elements that might otherwise hybridize to homologous repeats in the suppressive DNA 205 or target 200. In the FIG. 2, the probe signal would have a direct 1:1 correspondence with the single or low copy element 240 in the target 200.

Thus, one aspect of the invention provides a method of suppressing non-specific cross-hybridization between repetitive sequences present in nucleic acid probes and homologous repetitive sequences in target genomic nucleic acid. Generally, the method comprises identifying repetitive sequences in a representative genomic region, synthesizing suppressive nucleic acid derived from the identified repetitive sequences, and reacting the suppressive nucleic acid with a target nucleic acid. Preferably the suppressive nucleic acid comprises one or more sequence-defined PCR products selected from the group consisting of short interspersed elements, long interspersed elements, long terminal repeats. Alu elements, L1 elements, and DNA transposons. This reaction causes repetitive sequences in the suppressive nucleic acid to hybridize to homologous repetitive sequences in the target nucleic acid, thereby substantially blocking the repetitive sequences in the target nucleic acid from hybridizing with homologous repetitive sequences in a subsequently reacted nucleic acid probe, and consequently suppressing non-specific cross-hybridization between the repetitive sequences in the probe and homologous repetitive sequences in the target nucleic acid. This suppressive action is greatly enhanced by having the suppressive nucleic acid be substantially comprised of the identified repetitive sequences while also being substantially devoid of low copy sequences. Preferably, the suppressive nucleic acid is synthesized so as to be completely devoid of low copy sequences. In preferred forms, the target nucleic acid comprises low copy sequences. Preferably, the suppressive nucleic acid is synthesized to contain a plurality of repetitive sequences selected to correspond to repetitive sequences found adjacent to low copy sequences in one or more representative genomic regions. In some preferred forms, the method will include the further step of hybridizing the target nucleic acid with one or more probes containing low copy sequences homologous to low copy sequences in the target. In preferred forms, the probe will be substantially, and even more preferably completely, devoid of repetitive sequences. In other preferred forms, the method will include the step of conjugating the probe to a spectrally-encoded, polystyrene microsphere. Preferably, the probe will be labeled with a detectable moiety in order to enhance its utility. Some preferred detectable moieties include fluorophores, enzymatic conjugates, fluorophore-tagged nucleotides, fluorescently-labeled antibodies bound to antigen-bearing nucleotides, biotin-dUTP, digoxygenin-dUTP, and combinations thereof. This method, as well as the others described and taught herein, can be used in any procedure wherein cot-1 DNA was used or could be used including an assay selected from the group consisting of microarray hybridization assays, fluorescence in situ hybridization assays, and microsphere hybridization assays.

Another aspect provides a method of synthesizing suppression nucleic acid. Such a method generally includes the steps of identifying repetitive sequences in a representative genomic region; and synthesizing the suppression nucleic acid by synthesizing nucleic acid sequences hybridizable with the identified repetitive sequences but not hybridizable with low copy sequences near or within the representative genomic region. Preferably, the synthesized suppression nucleic acid is substantially free of low copy sequences. In some preferred forms, the method can also include the step of selecting certain identified repetitive sequences for synthesis as the suppression nucleic acid based on their proximity to a low copy sequence of interest. Preferably, such certain identified repetitive sequences are the ones in closest proximity to the low copy sequence of interest. Preferably, the synthesized suppression nucleic acid is free of sequences that are hybridizable with the low copy sequence of interest. Of course, a synthesized suppressive nucleic acid in accordance with the present invention can be used in a hybridization assay, and especially in a hybridization assay that could use Cot-1 or blocking DNA. Some preferred hybridization assays include fluorescence in situ hybridization assays, microarray assays, and microsphere hybridization assays.

Another aspect of the present invention provides a novel method of increasing hybridization specificity between low copy number nucleic acid probes and homologous regions in a target nucleic acid. Generally, such a method includes the steps of hybridizing repetitive elements in the target nucleic acid with homologous repetitive elements in a suppressive nucleic acid, wherein the suppressive nucleic acid comprises a plurality of repetitive elements and is synthesized or selected to be substantially, and more preferably, completely devoid of low copy number elements, and hybridizing low copy number elements in the target nucleic acid with homologous low copy number elements in one or more of the nucleic acid probes. In preferred forms, the repetitive elements in the suppressive nucleic acid are selected for having substantial homology to repetitive elements flanking low copy elements in one or more representative genomic regions. Even more preferably, the flanking repetitive elements are of moderate to high copy number and the low copy elements comprise single copy elements. Still more preferably, the probes are substantially devoid of repetitive elements.

Another aspect of the present invention provides a method for accurately quantitating nucleic acid sequence copy numbers. Generally, such a method comprising the steps of preparing a first, spectrally-encoded, fluorescent microsphere having a first spectral address, and a second, spectrally-encoded, fluorescent microsphere having a second spectral address, identifying a target genomic nucleic acid probe sequence by ascertaining the nucleotide-by-nucleotide sequence of a target nucleic acid sequence wherein the sequence of interest is suspected to reside, synthesizing a low copy target probe derived from the identified target genomic nucleic acid probe sequence, the target probe comprising at least one low copy element and being substantially devoid of repetitive elements, conjugating the target probe to the first microsphere, synthesizing a reference probe selected to hybridize to a reference nucleic acid sequence of the target nucleic acid sequence, conjugating the reference probe to a microsphere having a second spectral address, identifying repetitive sequences in a representative genomic region, synthesizing suppressive nucleic acid, the suppressive nucleic acid comprising sequences of sufficient homology to hybridize to the identified repetitive sequences, the suppressive nucleic acid substantially comprising repetitive elements and being substantially devoid of low copy elements, reacting the suppressive nucleic acid with a chromosomal target sequence, thereby causing repetitive elements in the suppressive nucleic acid to hybridize with homologous repetitive elements in the chromosomal target sequence, reacting the target probe to the chromosomal target sequence thereby causing low copy elements in the target probe to hybridize to homologous low copy elements in the chromosomal target sequence, reacting the suppressive nucleic acid with a chromosomal reference sequence containing the chromosomal target sequence thereby causing repetitive elements in the suppressive nucleic acid to hybridize to homologous repetitive elements in the chromosomal reference sequence, reacting the reference probe with the chromosomal reference sequence thereby causing the reference probe to hybridize to the chromosomal reference sequence, detecting the hybridized target probe via the first spectral address, detecting the hybridized reference probe via the second spectral address, and quantifying the detected target probe by comparing the response of the detected hybridized target probe with the response of the detected hybridized reference probe. In preferred forms, the suppressive DNA comprises repetitive elements with the repetitive elements corresponding to genomic repetitive elements adjacent to low copy elements in the target.

In another aspect of the present invention, a method for suppressing non-specific cross-hybridization between repetitive elements present in nucleic acid probes and homologous repetitive elements in target nucleic acid is provided. Generally, the method comprises the steps of hybridizing suppressive nucleic acid with homologous repetitive elements in a target nucleic acid containing one or more low copy elements. Preferably, the suppressive nucleic acid is synthesized or selected such that it contains a plurality of repetitive elements selected to correspond to one or more representative genomic regions containing single copy regions adjacent to moderate to high copy number repetitive element and is substantially devoid of low copy elements. Then, the target nucleic acid is hybridized with one or more probes containing low copy elements homologous to low copy elements in the target, the probes being substantially devoid of repetitive sequences.

In another aspect of the present invention, a method of suppressing non-specific cross-hybridization between low copy elements present in suppressive nucleic acid and homologous low copy elements in nucleic acid probes or target nucleic acid is provided. Generally, the method comprises the steps of identifying repetitive and low copy elements within and near the target nucleic acid, synthesizing suppressive nucleic acid sequences by selecting repetitive sequences from the target nucleic acid for inclusion in the suppressive nucleic acid while substantially avoiding the inclusion of low copy sequences in the synthesis process, and reacting the synthesized suppressive nucleic acid with the target nucleic acid such that the respective homologous suppressive nucleic acid and target nucleic acid elements hybridize with each other.

The present invention also provides a method of increasing the accuracy and reproducibility of assays using suppressive or blocking DNA (e.g. Cot-1 DNA) comprising the steps of selecting or synthesizing suppression nucleic acid that includes a plurality of repetitive elements but is substantially free of low copy sequences and using or substituting the selected or synthesized suppression nucleic acid in place of Cot-1 DNA.

In another aspect of the present invention, a method of suppressing adventitious hybridization of genomic target nucleic acid with a nucleic acid probe is provided. Generally, the method comprises the steps of preparing genomic target nucleic acid for hybridization by selecting a sequence or sequences in the genome corresponding to a sequence of interest; identifying low copy sequences within the target sequences of interest; synthesizing low copy probes homologous to the identified low copy target sequences, with the low copy probes being substantially devoid of repetitive sequences; identifying repetitive sequences adjacent to the target low copy sequences; synthesizing suppression DNA homologous to the target repetitive sequences, the suppression DNA substantially comprising repetitive elements, reacting the target nucleic acid with the suppression DNA so that the repetitive elements in the suppression DNA hybridize to homologous repetitive elements in the target nucleic acid; reacting the target nucleic acid with the low copy probes to hybridize low copy elements within the probes to homologous low copy elements in the target nucleic acid; and detecting the low copy probes in order to quantitate hybridization of the probe to the target, whereby instances of low copy elements within the target nucleic acid may be ascertained.

DEFINITIONS

Unless defined otherwise, all technical and scientific terms used herein have the same meaning as is commonly understood by one of ordinary skill in the art to which the invention belongs. All patents, applications, published applications and other publications and sequences from GenBank and other databases referred to herein are incorporated by reference in their entirety. If a definition set forth in this section is contrary to or otherwise inconsistent with a definition set forth in applications, published applications and other publications and sequences from GenBank and other data bases that are herein incorporated herein by reference, the definition set forth in this section prevails over the definition that is incorporated herein by reference.

As used herein, "a" or "an" means "at least one" or "one or more."

As used herein, "nucleic acid (s)" refers to deoxyribonucleic acid (DNA) and/or ribonucleic acid (RNA) in any form, including inter alia, single-stranded, duplex, triplex, linear and circular forms.

As used herein, "sequence" references to a nucleic acid sequence.

As used herein, the term "reference probe" means a probe specific for a locus in the genome, preferably from an autosomal sequence, that is severely damaging and preferably lethal in any other copy number but 2. The reference probe may be derived from any low or single copy chromosomal locus, so long as it has a normal chromosomal complement in the patient sample. In determination of genomic copy number for diagnosis of constitutional disease, reference probes will typically be of autosomal origin from one or more genes that are required to be expressed from two alleles during normal development. For determination of genomic copy number for diagnosis of neoplastic disease, reference probes are selected from chromosomal domains with a paucity of oncogenes and which have normal chromosomal complement.

As used herein, "label" refers to any chemical group or moiety having a detectable physical property or any compound capable of causing a chemical group or moiety to exhibit a detectable physical property, such as an enzyme that catalyzes conversion of a substrate into a detectable product. The term "label" also encompasses compounds that inhibit the expression of a particular physical property. The "label" may also be a compound that is a member of a binding pair, the other member of which bears a detectable physical property. Exemplary labels include mass groups, metals, fluorescent groups, luminescent groups, chemiluminescent groups, optical groups, charge groups, polar groups, colors, haptens, protein binding ligands, nucleotide sequences, radioactive groups, enzymes, particulate particles and a combinations thereof.

As used herein, "sample" refers to anything that may contain a target nucleic acid to be analyzed. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid, or the like. Biological tissues are aggregates of cells, usually of a particular kind together with their intercellular substance that form one of the structural materials of a human, animal, plant, bacterial, fungal or viral structure, including connective, epithelium, skin, muscle and nerve tissues. Examples of biological tissues also include organs, tumors, lymph nodes, arteries and collections of individual cell(s), for example, isolated from plasma, blood or urine or by collagenase treatment of solid tissues.

As used herein, "amplification" refers to a method for linearly duplicating a target analyte nucleic acid in a sample to improve assay sensitivity. As described herein, many different methods for amplifying nucleic acids are known in the art.

As used herein, "set" refers to a collection of microspheres harboring an identical spectral address conjugated either with a single 1c probe or a collection of 1c probes.

As used herein, "low copy" or "1c" refers to a sequences which will hybridize to ten or fewer sequence intervals in the target nucleic acid or locations in a genome. It is preferred that the copy number be 10 or fewer, more preferably 7 or fewer, still more preferably 5 or fewer, and most preferably 3 or fewer.

As used herein, "single copy" or "sc" refers to a nucleic acid or locations in a genome. Thus, the term will encompass sequences that are strictly unique (i.e., sequences complementary to one and only one sequence in the corresponding genome), as well as duplicons, and triplicons. The terms "single copy element" and "single copy sequence" may also be used to refer to such nucleic acid sequences.

As used herein, "highly reiterated" means present in more than 1000 copies.

As used herein, "sequence identity" refers to a relationship between two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988) Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994), Sequence Analysis in Molecular Biology, vonHeinge, G., Academic Press (1987); Sequence Analysis Primer, Gribskov, M. and Devereux J., eds., M. Stockton Press, New York (1991); and Carillo, H., and Lipman, D., SIAM J. Applied Math., 48: 1073 (1988). Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1): 387 (1984)), BLASTP, BLASTN and FASTA (Altschul, S. F. et al., J. Molec. Biol., 215:403410 (1990). The BLASTX program is publicly available from NCBI and other sources (BLAST Manual, Altschul, S. et al., NCBI, NLM, NIH, Bethesda, Md. 20894, Altschul, S. F., et al., J. Molec. Biol., 215:403410 (1990). These programs optimally align sequences using default gap weights in order to produce the highest level of sequence identity between the given and reference sequences. As an illustration, by a polynucleotide having a nucleotide sequence having at least, for example, 95% "sequence identity" to a reference nucleotide sequence, it is intended that the nucleotide sequence of the given polynucleotide is identical to the reference sequence except that the given polynucleotide sequence may include up to 5 differences per each 100 nucleotides of the reference nucleotide sequence. In other words, in a polynucleotide having a nucleotide sequence having at least 95% identity relative to the reference nucleotide sequence, up to 5% of the nucleotides in the reference sequence may be deleted or substituted with another nucleotide, or a number of nucleotides up to 5% of the total nucleotides in the reference sequence may be inserted into the reference sequence. Inversions in either sequence are detected by these computer programs based on the similarity of the reference sequence to the antisense strand of the homologous test sequence. These variants of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As used herein, a "repeat sequence" is a sequence which repeatedly appears in the genome of which the target DNA is a part, with a sequence identity between repeats of at least about 60%, more preferably, at least about 80%, and which is of sufficient length or has other qualities which would cause it to interfere with the desired specific hybridization of the probe to the target DNA, i.e., the probe would hybridize with multiple copies of the repeat sequence. Generally, speaking, a repeat sequence appears at least 10 times in the genome, has a repeat size ranging from 1 nucleotide to hundreds of nucleotides, the repeat units having lengths of at least 10 nucleotides to thousands of nucleotides. Repeat sequences can be of any variety, e.g., tandem, interspersed, palindromic or shared repetitive sequences (with some copies in the target region and some elsewhere in the genome), and can appear near the centromeres or chromosomes, distributed over a single chromosome, or throughout some or all chromosomes. Normally, with but few exceptions, repeat sequences do not express physiologically useful proteins. A "repeat sequence" may also be referred to as a "repetitive sequence" or a "repetitive element."

As used herein, a "short interspersed element," also referred to herein as a SINE, means a highly repetitive interspersed transposable element derived from RNA polymerase III transcripts with repeat units ranging in length from 75 bp to 500 bp in length. The most abundant class of SINE elements is the Alu family. Alu sequences are about 300 bp in length and are present in the human genome in approximately 500,000 copies.

As used herein, a "long interspersed element," also referred to herein as a LINE, means a highly repetitive interspersed transposable element derived from RNA polymerase I transcripts and with repeat units up to 7000 bp.

As used herein, a "long terminal repeat," also referred to herein as a LTR, means a large class of transposable elements which possess terminal direct repeats, typically 200-500 bp in length.

As used herein, a "MIR" repeat means a mammalian interspersed repetitive element which has a repeat unit length of at least 260 bp and is found in approximately 105 copies in the human genome.

As used herein, a "MER" repeat means a human moderately interspersed repetitive elements of unknown origin with copy numbers in the human genome ranging from 100's to 1000's.

As used herein, moderately repetitive DNA means repetitive sequences distributed in the uniformly in the human genome, present in 10 to 1000 copies and are 150 to 300 bp in repeat length. One example is the Alu family.

As used herein, highly repetitive DNA means short repetitive sequences 5 to 300 bp in length that present in up to $10^5$ copies in the human genome. One example is satellite DNA.

As used herein, the terms, "DNA transposons" or "transposons" refer to sequences of DNA that can move from one location to another within the genome. These sequences may also be referred to as "mobile genetic elements." Movement of transposons is typically referred to as transposition.

BRIEF DESCRIPTION OF THE DRAWING FIGURES

FIG. 3 is a diagram illustrating potential structures produced in QMH hybridization in the presence of $C_o$t-1 DNA;

DETAILED DESCRIPTION OF THE PREFERRED EMBODIMENTS

Figure 1:
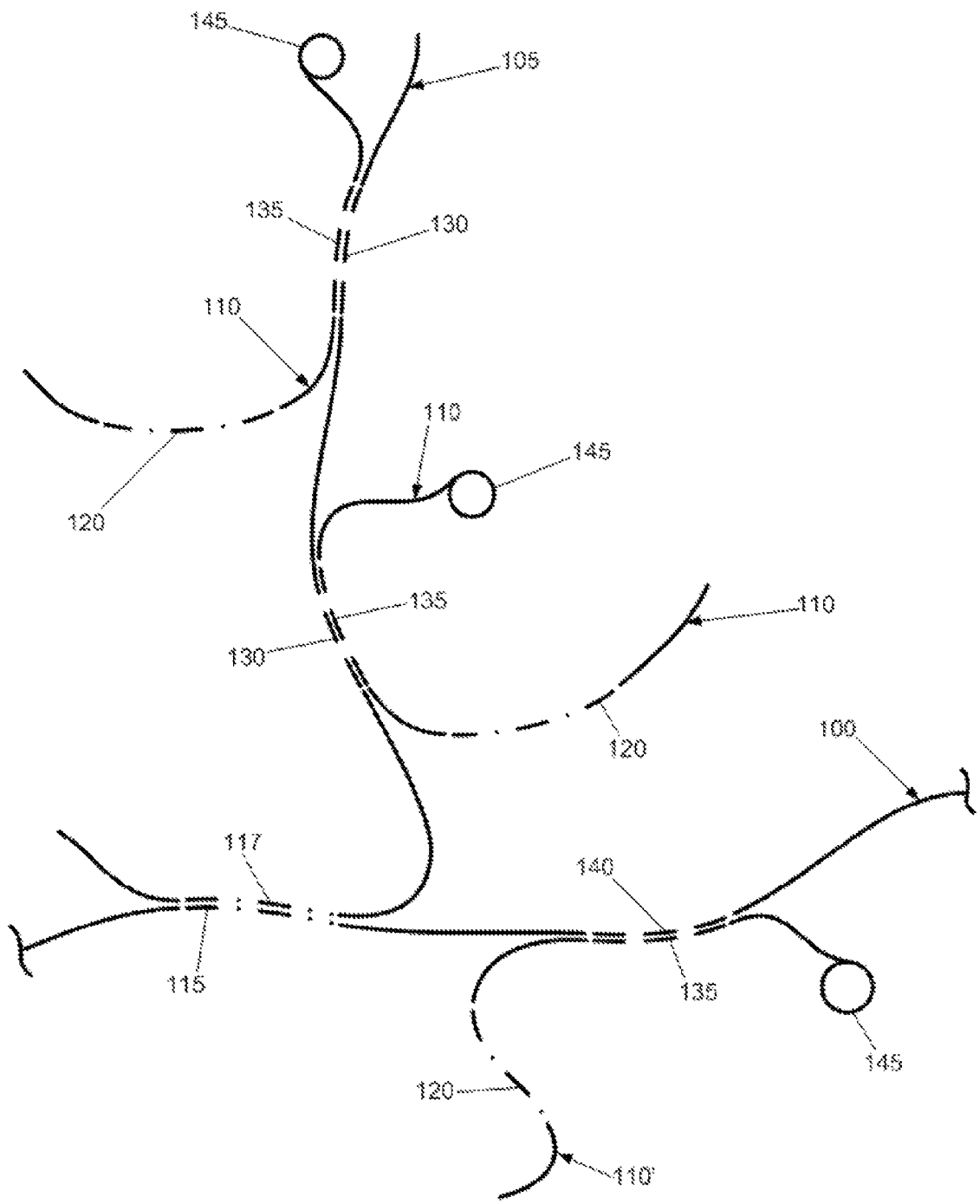
FIG. 1 is a diagram illustrating hybridization of probes to single copy elements in $C_o$t-1 DNA.
Figure 2:
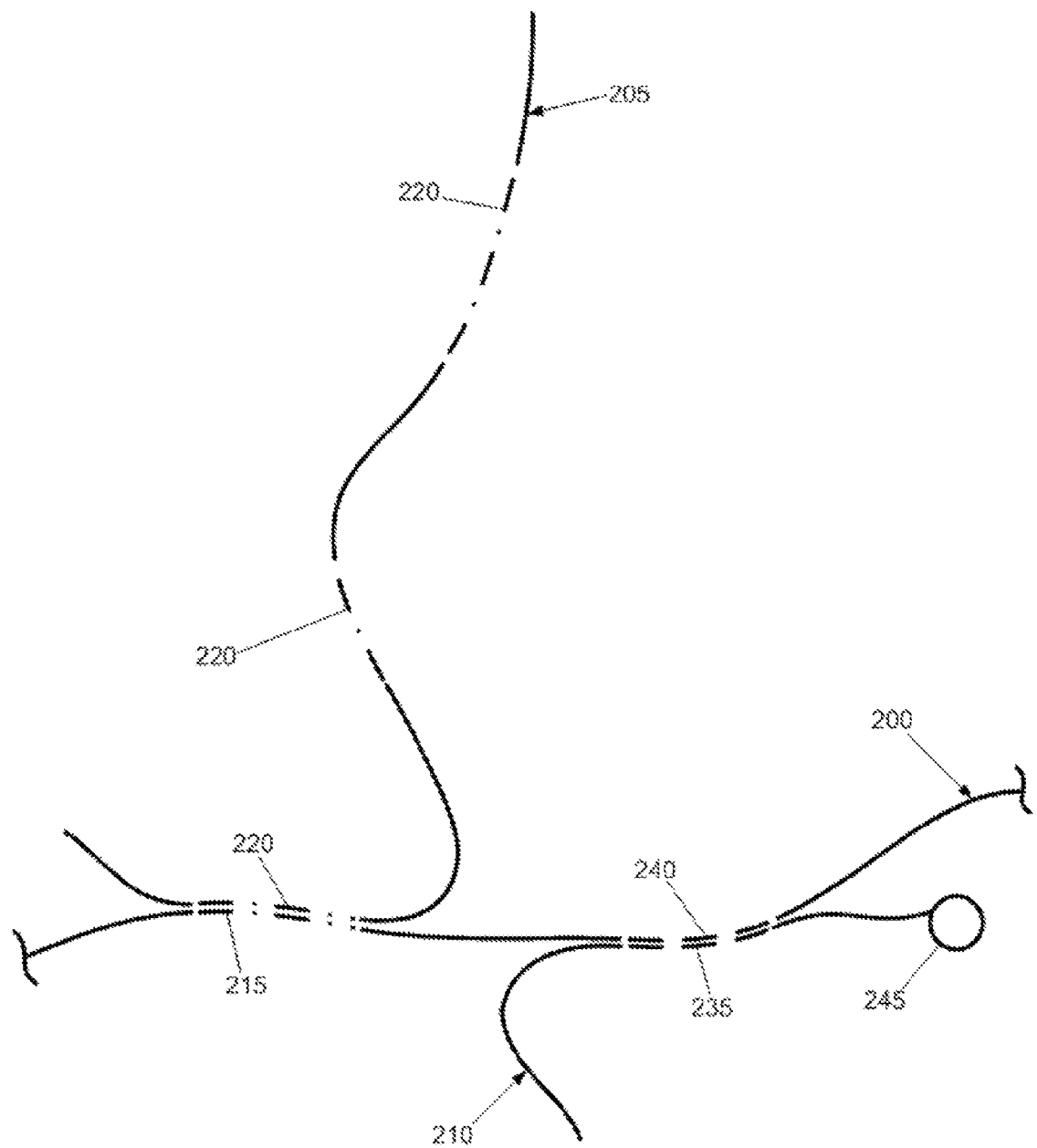
FIG. 2 is a diagram illustrating hybridization of suppression DNA to a repetitive sequence in target nucleic acid.

The following example sets forth preferred embodiments of the present invention. These embodiments demonstrate hybridization of single (or low) copy probes to genomic target previously hybridized to synthetic DNA containing repeat elements but not single or low copy elements. However, these embodiments are for illustrative purposes only and the disclosure herein should not be construed as a limitation upon the scope of the present invention.

EXAMPLE

Materials and Methods

Quantitative Microsphere Hybridization (QMH)

Probe Selection Synthesis, and Microsphere Conjugation

The probes are in the form of labeled nucleic acid fragments or a collection of labeled nucleic acid fragments whose hybridization to a target sequence can be detected. The labeled probes may be used with any nucleic acid target that contains sequences homologous to sequences in the probe. These target sequences may include, but are not limited to chromosomal or purified nuclear DNA, heteronuclear RNA, or mRNA species that contain single copy sequences as integral components of the transcript. In the ensuing detailed explanation, the usual case of a DNA target sequence and DNA probes is discussed; however, those skilled in the art will understand that the discussion is equally applicable (with art-recognized differences owing to the nature of the target sequences and probes) to other nucleic acid species.

An important characteristic of the preferred probes of the invention is that they are made up of "low copy", "single copy", or "unique" DNA sequences which are both complementary to at least a portion of the target DNA region of interest and are essentially free of sequences complementary to repeat sequences within the genome of which the target region is a part. Accordingly, a probe made up of a single copy or unique sequence is preferably complementary to three or fewer sequences, and preferably only one sequence, in the corresponding genome.

Low copy, or mixed low copy and repetitive, sequence probes were designed as previously described[14, 15, 16, 20]. In preferred forms, the present invention utilizes low or single copy hybridization probes specially designed to hybridize to a unique locus in the haploid genome sequence with high specificity. The method for probe selection and synthesis is disclosed in U.S. Pat. Nos. 6,828,097 and 7,014,997, the teachings and content of which are hereby incorporated by reference. These initial steps require knowledge of the sequences of both the target and genomic repeats, information that is increasingly available owing to the Human Genome Project and related bioinformatic studies. Readily available computer software was used to derive the low, or preferred single, copy sequences.

In order to develop probes in accordance with the invention, the sequence of the target DNA region must be known. The target region may be an entire chromosome or only portions thereof where rearrangements have been identified. With this sequence knowledge, the objective is to determine the boundaries of single copy or unique sequences within the target region. This is preferably accomplished by inference from the locations of repetitive sequences within the target region. Normally, the sequence of the target region is compared with known repeat sequences from the corresponding genome, using available computer software. Once the repeat sequences within the target region are identified, the intervening sequences are deduced to be low or single copy (i.e., the sequences between adjacent repeat sequences). Optimal alignment of the target and repetitive sequences for comparison may be conducted by the local homology algorithm of Smith et al., Adv. Appl. Math., 2:482 (1981), or by the homology alignment algorithm of Needleman et al., J. Mol. Biol., 48:443 (1970).

Preferably, at least two different probe sequences are selected and synthesized. At least one set of probes should be selected and synthesized for recognition of a particular nucleic acid sequence wherein the abnormality, if present, would residue (test probe), and another set of probes should be selected and synthesized for recognition of a reference sequence (reference probe). The low copy probes should be at least about 60 base pairs and generally nor more than 2500 base pairs in size. Preferably, the probes are between 60 and 1000 base pairs, more preferably between about 80-500 base pairs and most preferably between about 90-100 base pairs. It was found that microspheres conjugated to low copy probes of about 100 base pairs produced well-defined mean fluorescence distributions and consistently higher secondary fluorochrome mean fluorescence intensity values, and thus more precisely reflected the actual copy numbers. The shorter probe conjugates are also more stable and can be used in hybridization reactions for more than two months after conjugation when properly stored, preferably in the dark and at about 4° C. This results in less lot-to-lot variation in labeled microsphere stocks, thereby reducing the effort required to conjugate quantify and qualify probe-conjugated microspheres. Longer conjugated probes showed degraded hybridization efficiency within two weeks after conjugation.

The probes used in this example include probes with sc intervals (i) ABL1a (May 2004, chr9: 130623551-130625854) with divergent AluJo/Sx/L2 repeats and (ii) ABL1b (chr9: 130627353-130628735) with divergent AluJo repeats from within ABL1, designed and validated previously[13, 14], (iii) a 1823 bp chromosome 9 probe with Alu/Mer1 repetitive sequences, ABL1AluMER1 (chr9: 130621702-130623525), (iv) a 98 bp sc segment of a TEKT3 intron (Chr17: 15149108-15149206) and (v) a 101 bp sc segment of a sPMP22 intron (Chr17: 15073475-15073576), (vi) a 93 bp sc segment of a HOXB1 intron (Chr17: 43964237-43964330). Probes for genomic reconstruction experiments included: (vii) HOXB1b (chr17: 43963396-43965681) and (viii) C1QTNF7 (chr4:15141452-15141500). Repetitive sequences found within probes were defined as divergent, based on percent sequence differences (>12%), percent deletion (>4%), and/or percent insertion (>4%) relative to consensus family members (on the Internet at girinst.org).

Coupling of Probes to Microspheres

Probes were synthesized and coupled to microspheres as previously described[13, 20]. During synthesis, the probes can be amine-tagged, depending upon the particular conjugation reaction, for conjugation to spectrally-distinct microspheres. Preferably, the probes are conjugated to the microspheres via a modified carbodiimide reaction.

Fluorescent microspheres, each with distinct spectral addresses (designated L1-L9; Duke Scientific, Palo Alto Calif.) and coated with approximately 200,000 carboxy-sites, were conjugated individually to different 1c probes. Purified amino-modified 1c probes were couples to the carboxylated microspheres via a modified carbodiimide coupling procedure (Dunbar et al, 2003; Fulton et al., 1997). Each probe was initially heat denatured and then snap-cooled on ice. Approximately $3.125 \times 10^5$ microspheres with identical spectral characteristics were pipetted into a 1.5 mL microcentrifuge tube (USA Scientific, Ocala, Fla.), centrifuged for 2 minutes at 10,000 g, and drained of supernatant. 150 µL of 0.1M MES buffer (2-(N-morpholino)ethanesulfonic acid) pH 4.5 was added to each tube and the microspheres were vortexed briefly followed by centrifugation for 2 minutes at 10,000 g.

The supernatant was removed and the microspheres were resuspended by vortexing in 80 μL of 0.1M MES. A single 1c probe (0.5 nmol) was added to each tube and mixed by vortexing. A 1.25 μL volume of fresh 10 mg/ml solution of 1-ethyl-3-3-dimethylaminopropyl carbodiimidehydrochloride (EDC) was added and the reaction was vortexed briefly and incubated in the dark for 30 minutes with occasional mixing. Mixing and incubation of EDC was repeated twice, using 1.25 μL of freshly prepared EDC solution each time. The reaction was stopped by the addition of 500 μL 0.02% Tween20 followed by vortexing and centrifugation for 2 minutes at 10,000 g. Following removal of the supernatants, 250 μL of 0.1% SDS was added to each tube, vortexed, and then centrifuged at 10,000 g for 2 minutes. The supernatant was carefully removed 25 μL of 0.1M MES pH4.5 was added, and the tube was vortexed and stored in the dark at 4° C. Coupled microsphere concentrations were quantitated by adding 1 μL of each microsphere to 100 μL of 1×PBS and analyzing on the FACSCalibur flow cytometer (Becton Dickinson, San Jose, Calif.) using conditions given below.

Other methods for coupling nucleic acids to microspheres have been developed that are equivalent in scope to the instant method. Another common method for conjugating DNA to microspheres binds strepatividin-coated beads to probes containing a modified nucleotide with a biotin moiety at the 5' terminus. Gold nanoparticles have been conjugated to thiol-modified nucleic acids in U.S. Pat. No. 6,361,944. Protein-nucleic acids have been conjugated to beads in U.S. Pat. Nos 6,468,546; 6,838,243; 6,833,246; 6,828,146; and 6,828,142. Conjugation of oligonucleotides to microspheres has also been carried out via an electrophilic tether, namely N-chloroacetamidohexyl phosphoramidite reagent (Guzaev, et al Bioorg Med Chem Lett. 1998 Dec. 15; 8(24); 3671-6). DNA has also been conjugated to semiconductor nanocrystalline particles (Taylor, J. R., Fang, M. M., & Nie, S. M. Probing specific sequences on single DNA molecules with bioconjugated fluorescent nanoparticles. *Anal. Chem.* 72, 1979-1986, 2000; W. Z. Guo, J. J. Li, Y. A. Wang, X. G. Peng. Conjugation chemistry and bioapplications of semiconductor box nanocrystals prepared via dendrimer bridging. *Chem. Mater.* 15, 3125-3133 (2003), and U.S. Pat. No. 6,630,307). In a preferred embodiment, the microspheres are internally dyed, fluorescent, polystyrene beads with various spectral addresses, and are conjugated to low copy probes such that various combinations of low copy probe-conjugated beads result, wherein the reference probes are designated with a distinct spectral address. The different spectral addresses are recognized by the flow cytometer and allow for multiplexed reactions with various low copy probes attached to different microsphere sets.

Genomic Target Preparation

Genomic template (the target nucleic acid sequence) was prepared using methanol-acetic acid fixed cell pellets derived from cytogenetic preparations of bone marrow samples as previously described[13, 20]. Unlike other methods, the target sequence is not pre-selected or amplified. Therefore, in the present invention an entire copy of a genome (or transcriptome) can be hybridized for analysis. Depending on the source and condition of the sample, the DNA (or RNA) is extracted from the cells and, if necessary, can be replicated in vitro using any conventional method. Preferably, the nucleic acid is replicated in vitro using a GenomiPhi kit (Quake, Valencia Calif.), which utilizes less than one rig of sample nucleic acid and requires less than 20 minutes hands-on time. The DNA is then labeled by any conventional means, preferably by a direct labeling step during in vitro replication or by an indirect labeling system consisting of a label and a reporter molecule that has an affinity for the label. The nucleic acid target is labeled with an identifying label such as a fluorophore, and enzymatic conjugate, or one selected from the group consisting of biotin or the moieties recognized by avidin, strepavidin, or specific antibodies. There are several types of non-isotopic identifying labels. One type is a label which is chemically bound to the nucleic acid target and serves as the means for direct identification. An example of this would be a fluorochrome moiety, which upon application of radiation of proper wavelengths will become excited into a high energy state and emit fluorescent light. Directly labeled fluorescent nucleotides such as Cy3-dUTP are known in the art and would be suitable forms of labeling of target DNA for use with the instant invention. Other methods of direct labeling of DNA would also be suitable (an example would be the amino-allyl labeling marketed as the Ulysses method (Kreatech, Netherlands), however in such instances the genome DNA would have to be fragmented (by sonication, Daze I, shearing, or other enzymatic digestion) to a suitable size for hybridization prior to addition of the labeled target to probe conjugated microspheres. In a preferred embodiment, the nucleic acid is directly labeled during in vitro replication using biotin-dUTP or digoxygenin-dUTP and resulting labeled sample is sonicated to yield fragments ~300 bp to 1 kbp in length. The nucleic acid target can also be labeled by nick translation using a modified or directly labeled nucleotide (Rigby et al., *J. Mol. Biol.*, 113: 237-251, 1977) in the conventional manner using a reactant comprising the identifying label of choice (but not limited to) conjugated to a nucleotide such as dUTP or dATP. The fragments are either directly labeled with fluorophore-tagged nucleotide or indirectly labeled by binding the labeled duplex to a fluorescently-labeled antibody that recognizes the modified nucleotide that is incorporated into the fragment as described below. Nick translations (100 μL) utilize endonuclease-free DNA polymerase I (Roche Molecular Biochemicals and DNase I (Worthington Chemical). Each fragment is combined with DNA polymerase I (4 units/microgram DNA), DNase (0.01-3 microgram/100 μL reaction), labeled nucleotide (0.05 mm final) and nick translation buffer. The reaction is performed at 15° C. for 60 minutes and yields a variety of labeled probe fragments of different nucleotide sizes in ~300 to 1000 bp size range. Alternatively, biotin-dUTP or digoxygenin-dUTP can be incorporated during the in vitro replication procedure and resulting labeled sample can be treated with DNAse I or sheared by some other method to yield fragment ~300 bp to 1 kb in length. Other methods for labeling and detecting nucleic acids in common use may be applied to the detection of low copy DNA conjugated microspheres of the present method. These include fluorochrome labels and fluorescent compositions such as energy transfer groups, conjugated proteins, antibodies, or antigens.

More specifically, one μg of genomic and pUC19DNA was nick-translated with biotin-16 dUTP to obtain products 100 bp-350 bp and 50 bp-300 bp in length, respectively[17]. One μg of each $C_o t$-1 DNA (from manufacturers I and R) was nick-translated with digoxygenin-11 dUTP to obtain products 50 bp-300 bp.

Hybridization Reactions and Flow Cytometry

Labeled DNA (50 ng) was diluted in 40 μL 1.5×TMAC hybridization buffer (3-mol/L tetramethylammonium chloride, 50 mmol/L Tris-HCl, pH8.0, 1 g/L Sarkosyl) containing 10,000 probe-coupled microspheres. Reactions were assembled with the components listed in Table 1.

TABLE 1

Quantitative Microsphere Hybridization (Mean Fluorescence)

| Reaction | Target DNA* | Repeat-blocking agent (ng)** | Probe | Geometric Mean FL2-SPE* | FL1-FITC** |
|---|---|---|---|---|---|
| Effects of Cot-1 on hybridization intensity levels affected by genomic location of probe ||||||
| 1 | Genomic | 0 | ABL1a | 105.62 | N/A |
| 2 | Genomic | Cot-1 (50) | ABL1a | 235.19 | N/A |
| 3 | Genomic | 0 | PMP22 | 433.76 | N/A |
| 4 | Genomic | Cot-1 (50) | PMP22 | 469.27 | N/A |
| 5 | Genomic | 0 | TEKT3 | 642.68 | N/A |
| 6 | Genomic | Cot-1 (50) | TEKT3 | 734.04 | N/A |
| 7 | Genomic | 0 | HOXB1 | 890.91 | N/A |
| 8 | Genomic | Cot-1 (50) | HOXB1 | 821.35 | N/A |
| 9 | Genomic | 0 | HOXB1 | 332.94 | N/A |
| 10 | Genomic | Cot-1 (50) | HOXB1 | 279.1 | N/A |
| 11 | Genomic | 0 | HOXB1 | 2034.76 | N/A |
| 12 | Genomic | Cot-1 (50) | HOXB1 | 1727.8 | N/A |
| Dual detection of genomic target and Cot-1 DNA in single reactions ||||||
| 13 | Genomic | 0 | ABL1a | 187.02 | 5.67 |
| 14 | Genomic | Cot-1 (50) | ABL1a | 390.79 | 282.48 |
| 15 | pUC19 | Cot-1 (50) | ABL1a | 5.88 | 6.34 |
| Dilution series of Cot-1 DNA in hybridization reactions ||||||
| 16 | Genomic | Cot-1 (50) | ABL1b | 304.91 | 77.8 |
| 17 | Genomic | Cot-1 (100) | ABL1b | 407.61 | 141.41 |
| 18 | Genomic | Cot-1 (150) | ABL1b | 449.94 | 234.44 |
| Hybridization experiments with recovered products ||||||
| 19 | Genomic | 0 | ABL1a | 153.12 | 5.37 |
| 20 | Genomic | Cot-1 (50) | ABL1a | 339.8 | 191.57 |
| 21 | Genomic$^R$ | 0 | ABL1AluMER1 | 4.55 | 3.27 |
| 22 | Genomic$^R$ | Cot-1 (50)$^R$ | ABL1AluMER1 | 5.36 | 35.32 |
| Genomic reconstruction experiments: ||||||
| 23 | PCR | 0 | C1QTNF7 | 270.72 | N/A |
| 24 | PCR | C1QTNF7LTR (500) | C1QTNF7 | 270.42 | N/A |
| 25 | PCR | Cot-1 (50) | C1QTNF7 | 321.02 | N/A |
| 26 | Genomic | 0 | C1QTNF7 | 1001.83 | N/A |
| 27 | Genomic | C1QTNF7LTR (500) | C1QTNF7 | 806.59 | N/A |
| 28 | Genomic | Cot-1 (50) | C1QTNF7 | 1226.61 | N/A |
| 29 | Genomic | 0 | ABL1a | 565.73 | N/A |
| 30 | Genomic | ABL1aAlu, ABL1aL2 (500) | ABL1a | 554.27 | N/A |
| 31 | Genomic | Cot-1 (50) | ABL1a | 1205.01 | N/A |
| 32 | PCR | 0 | HOXB1b | 94.66 | N/A |
| 33 | PCR | HOXB1AluL1 (500) | HOXB1b | 28.41 | N/A |

$^R$Recovered products from previous hybridization assay
*Nick-translated using biotin-16dUTP and detected using SPE on FL2, 50 ng per reaction Hybridization and detection of reactions were carried out as previously described[13, 20]. The conditions for the hybridization reaction are dependent on the particular nucleotide composition and the length of each low copy probe, and are easily determined by those of skill in the art. For hybridization, the sample sequence is diluted in a hybridization buffer solution containing the low copy probe-conjugated microspheres. The amount of probe-conjugated microspheres to be utilized will depend upon the amount of sample tested. Preferably, about 5 pg to 1 µg of sample, more preferably about 24-100 ng of sample, still more preferably about 30-70 ng, yet more preferably about 40-60 ng of sample, and most preferably about 50 ng of sample, is analyzed per hybridization reaction. Accordingly, the buffer solution preferably contains about 2,000-10,000 probe-conjugated microspheres, more preferably 2,000-6,000 probe-conjugated microspheres, still more preferably about 4,500-5,500 probe-conjugated microspheres, and most preferably about 5,000 probe-conjugated microspheres for each set to be hybridized. Once diluted, the hybridization reaction is heat denatured, preferably at about 95° C. and then hybridized overnight at a suitable hybridization temperature, preferably, at about 45 to 51° C. depending upon the probe nucleotide composition and length. The hybridized microspheres are then washed and centrifuged to remove unhybridized sequence.

The supernatant is removed and the hybridized sample is stained or labeled with an amount of a modified reporter molecule or other suitable label, preferably one which acts as a secondary fluorochrome, to detect the labeled sample hybridized to the low copy probe-conjugated microspheres. The preferred reporter molecules are phycoerythrin-labeled streptavidin or anti-digoxigenin fluoroscein, which detect and bind the preferred target sequence labels, biotin and digoxigenin, respectively. The hybridized and labeled/stained sample is incubated at the same temperature used for the hybridization reaction, for a period of time sufficient for the reporter molecule to detect and bind the labeled target sequence. Afterwards, the sample is washed to remove residual stain. The samples are centrifuged, the supernatant removed and the stained hybridized microspheres are resuspended in an amount of hybridization buffer.

Before analysis by flow cytometry, the hybridized samples can be diluted depending upon the flow cytometer manufacturer's instructions. Preferably, about 2,000-6,000 microspheres of each set are analyzed per reaction, more preferably about 4,500-5,500 microspheres, and most preferably about 5,000 macrospheres per set are analyzed per reaction. However, the amount of sample to be analyzed may depend upon the particular flow cytometer utilized for analysis. Calibration and operating settings for the flow cytometer can be modified in a number of ways without undue experimentation, by those skilled in the art, to determine the optimal ranges for measuring a particular hybridization assay. These parameters will also depend upon the software employed for analysis. Fluorescent bead standards are widely available and can be used to calibrate the intensity of different fluorochrome detection channels of the flow cytometer. The instrument can also be calibrated with fluorescent reference standards based on surface-labeled beads calibrated in molecules of equivalent soluble fluorochrome (MESF) units. Photomultiplier tube (PMT) voltage settings and thresholds for forward scatter, side scatter, flow rate, and various detection channels should preferably be optimized to minimize differences between fluorescence intensities of two different probes hybridized to a single patient sample with a normal genotype. Non-optimal voltage parameters are readily apparent and result in broad fluorescence peaks or non-linear data, whereas optimal parameters preferably result in tightly clustered microspheres with different spectral addresses when visualized using a side scatter plot. Preferably, these settings are determined from derived fluorescence measurements of arithmetic mean, geometric mean, median and peak channel.

Reactions were denatured for 3 minutes and hybridized overnight at 50° C. Hybridized microspheres were washed and stained with reporter molecule, streptavidin phycoerythrin (SPE; Molecular Probes) and/or anti-digoxygenin-fluorescein isothiocyanate (FITC; Molecular Probes). The hybridized samples were analyzed by flow cytometry (FACSCalibur, Becton Dickinson, San Jose, Calif.), using dual laser detection, whereby the cytometer co-detects the spectral addresses of the microspheres and the secondary fluorochrome bound to the sample sequences in order to identify and quantify the hybridized probes. The signal of each sample sequence, hybridized to its complementary probe-conjugated microsphere, is determined by quantifying the fluorescence intensity of the secondary fluorochrome attached to the sample sequence. Compatible microsphere spectral addresses are selected to minimize overlap with the emission wavelengths of any unbound secondary fluorochrome (reporter molecule). This can be confirmed by comparison with results obtained from otherwise identical unconjugated and unhybridized microspheres. A negative control may also be maintained using a reaction tube containing all of the components except for the sample nucleic acid in order to determine background fluorescence in the secondary fluorochrome detection channel. Preferably, the system is flushed with distilled water between runs to remove any residual microspheres.

Approximately 5,000 microspheres were analyzed per reaction. Hybridization was quantified from the SPE and/or FITC mean fluorescence intensity (measured in channels FL2 and/or FL1, respectively), which corresponds to the quantities of genomic target (FL2) and of $C_o t$-1 DNA (FL1) bound by probe. Calibration studies with conjugated probes and labeled targets containing identical sequences demonstrated that changes in mean fluorescence intensity were linearly related to the amount of target hybridized. The FL1 and FL2 channel background fluorescence was separately determined in each hybridization experiment using a negative control containing all reaction components except target DNA.

Optimal PMT voltages were set as described previously; data collection and analysis were performed with manufacturer-supplied CellQuest software[13,20]. Optimal photomultiplier tube voltage settings were determined by selecting photomultiplier voltage tube settings that minimized differences between fluorescence intensities of two different probes hybridized to a single patient DNA sample with a normal genotype. These settings were determined from instrument-derived fluroescence measurements (CellQuest; Becton Dickinson) of arithmetic mean, geometric mean, median and peak channel. Typical photomultiplier tube voltage settings for the FACSCalibur instrument were FSC (forward scatter)= E00 (no signal amplification), SSC (side scatter)=344 V, FL1=727V, FL2=640V, FL3=300V, and FL4=600V. Thresholds for FSC, FL1, FL2, and FL3 were set at the default of 52 V. The FSC threshold was selected as the primary parameter and had a value of 52 V and the secondary parameter was set at SSC with a value of 125 V. The flow rate was set on low and the sheath fluid used was FACsFlow (Becton Dickinson). The system was flushed between runs with 2-5 mL of distilled water to remove any residual microspheres. CellQuest was used for data collection and analysis. Analysis of data was also performed using WinMDI2.8 flow cytometry package (WinMDI, J. Trotter, Salk Institute, La Jolla, Calif.)

Recovery of Probe-Hybridized DNA Fragments

Aliquots (35 μL) of genomic hybridizations with ABL1a (Table 1: reactions 19 and 20) were washed with 250 μL 0.1×SSC 1% SDS and pelleted by centrifugation (13,000×g), and repeated twice. The hybridized genomic sequences were heat denatured at 95° C. for 5 minutes and snap-cooled followed by centrifugation (13,000×g) at 4° C. for 3 minutes. Recovered sequences were used as target for QPCR and for hybridization to microsphere-coupled ABL1AluMER1 (Table 1: Reactions 21 and 22).

Synthetic Repetitive DNA

Figure 4:
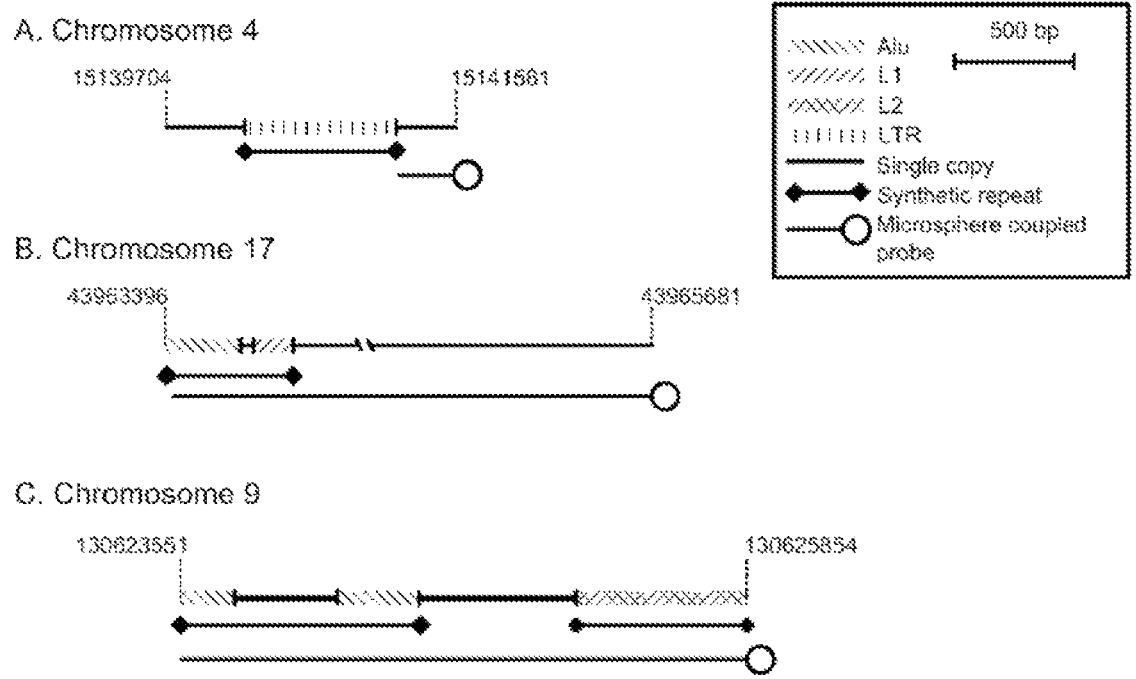
FIG. 4 is a diagram illustrating synthetic repetitive products and probes used in suppression or cross-hybridization to genomic templates.

Synthetic repetitive DNA was prepared from genomic regions selected based on the families of repetitive sequences contained within them, since each is enriched in the $C_o t$-1 manufacturing process. However, any representative genomic region containing sc regions adjacent to moderate to high copy number repetitive elements could have been employed. To demonstrate that repeat elements in genomic probes could be suppressed at locations beyond the desired target interval, a probe was prepared containing a 1.1 kb LTR element centered between two 400 bp sc regions on chromosome 4p (chr4: 15139704-15141581) located upstream of the C1QTNF7 gene (FIG. 4, A). Subsequently, repetitive sequences situated within the ABL a probe region for blocking this repeat element were synthesized; ABL1a from chromosome 9 contains a 280 bp AluJo repeat, a 300 bp AluSx repeat, and an 830 bp L2 element segment (FIG. 4, C). A 2286 bp segment on chromosome 17q located 5' of HOXB1 containing a 306 bp AluSx repeat and 154 bp L1 truncated sequence (chr17: 43963396-43965681) was also used as a probe (FIG. 4, B). Primers that amplified unique sequences immediately flanking these repetitive elements (Table 2: HOXB1AluL1 and C1QTNF7LTR) were developed for PCR amplification of each repeat sequence and of the target product (Table 2. HOXB1b and C1QTNF7). Genomic DNA (Protegee) probes were amplified using Pfx (Invitrogen). Amplification products were then electrophoresed and extracted by micro-spin column centrifugation. Probes were conjugated to microspheres via a modified carbodiimide reaction as previously described[13, 20]. Hybridization reactions (Table 1: Reactions 23-33) evaluated the effect of the synthetic repetitive PCR products hybridized to homologous PCR product, and/or genomic DNA, in the presence and absence of $C_o$t-1 DNA. Reactions were hybridized, washed, stained with SPE, and then analyzed by flow cytometry.

Quantitative PCR

QPCR and data analysis were performed using the Chromo4 quantitative PCR system (Bio-Rad Laboratories, Hercules, Calif.). Primers and amplified intervals were verified for unique genomic representation using BLAT[18] (found on the Internet at genome.ucsc.edu/cgi-bin/hgBlat) and BLAST (Table 2). BLAT is a computer software tool that includes a sequence alignment algorithm and an index of vertebrate sequences to identify regions in the human genome of likely homology to the queried sequence. BLAT is an alignment tool similar to BLAST, only structured differently since BLAT works by keeping an index of an entire genome in memory, whereas the target database for BLAST includes Genbank sequence collections. Each 50 μL reaction contained 0.5 μM of each primer, 50 ng $C_o$t-1 template or positive control human genomic DNA (Promega), and 25 μL 2XQTSybrG master mix (Qiagen). Genomic DNA was nicked using DNAse to generate fragments from 50 bp-300 bp, and a negative control contained all reaction components except for DNA. Thermal cycling conditions were 95° C. for 15 minutes, 45 cycles of amplification (94° C. for 15 seconds, 61° C. for 30 seconds (data acquisition), 72° C. for 30 seconds), followed by 72° C. for 5 seconds with a decrease in temperature by 20° C. every second for the generation of a melt curve. A calibration curve used to determine the amount of input target sequence in the recovered genomic template was generated by varying the amounts of normal genomic template (1 ng, 2 ng, 4 ng, 10 ng, and 20 ng) and by determining the $C_T$ values for each reaction.

The composition of sequences recovered from the ABL1a product hybridization (1 μL; Table 1: Reactions 21 and 22) was determined by QPCR. Primer sets utilized several amplified sequences from within the ABL1 region, which were not necessarily homologous to this probe, including: ABL1a and ABL1c (chr9: 130709665-130711469), ABL1d (chr9: 130699324-130700596)) as well as primers specific for other unlinked genomic regions such as DNJA3Alu (chr16: 4421138-4421200), containing an Alu repeat located 5' of the DNAJ3 gene, TEKT3, and HOXB1 (Table 2). Reactions were performed as described above. A positive control (human genomic DNA) was run for each primer set to represent the initial quantity of genomic DNA originally added to QMH reactions (50 ng). Molar ratios of target sequences recovered from QMH were determined from the quantity of initial template in test samples (interpolated from its $C_T$ value cross-referenced against the standard calibration curve) in the presence and absence of $C_o$t-1 DNA.

TABLE 2

Probes and primers used in this study

| Probe | Chromosome | Primer Name | Sequence (5'->3') |
|---|---|---|---|
| ABL1a | 9 | ABL1aF | GTGGCTTATGCCTGTAAT TTCACA (SEQ ID NO. 1) |
| | | ABL1aR | AGAGACAGGGTCTTCTTA TGTTGC (SEQ ID NO. 2) |
| ABL1b | 9 | ABL1bF | ATTTGGAAAGATTATATC CATCTACTTAATGC (SEQ ID NO. 3) |
| | | ABL1bR | ACAAACCTACCTACGTTT CAACACTCTCTT (SEQ ID NO. 4) |
| ABL1c | 9 | ABL1cF | GCTTTATGAACTAGCTGA TTTAGTTTGCTC (SEQ ID NO. 5) |
| | | ABL1cR | CTCAATCTCTCTTTTATC TGTTTTGTCCATTG (SEQ ID NO. 6) |
| ABL1d | 9 | ABL1dF | TAGTTAATTTAGAAGGTT TAAATCACGAGAA (SEQ ID NO. 7) |
| | | ABL1dR | CTAATTTTTAAATGTGTG AATGCAATTTT (SEQ ID NO. 8) |
| RRP4-1.6a | 9 | RRP4-1.6a5'F | CAGAGGAAGGAAGACGTA GTGAAC (SEQ ID NO. 9) |
| | | RRP4-1.6a5'R | GCTGAACCAAGCAGACAC AG (SEQ ID NO. 10) |
| RRP4-1.6a | 9 | RRP4-1.6aF | ATGGGAGCTTGGATAAGA GATG (SEQ ID NO. 11) |
| | | RRP4-1.6aR | CTATACCCTGAGGCGATA ATGTTC (SEQ ID NO. 12) |
| RRP4-1.6a | 9 | RRP4-1.6a3'F | AGCAGATCAGACATACAG GTCCAA (SEQ ID NO. 13) |
| | | RRP4-1.6a3'R | GGCCACCGTAAGTTACAA GACC (SEQ ID NO. 14) |
| ABL1AluMer1 | 9 | ABL1AluMER1-F | C-12-Amine-CCTCTTC GGGGTAGAGTTTCGCTCT (SEQ ID NO. 15) |
| | | ABL1AluMER1-R | CTCAGGCCCTTGTCACAC TCTTGAA (SEQ ID NO. 16) |
| DNJA3Alu | 16 | DNJA3Alu-F | CTCCTGTCCGTGTTCTCT GC (SEQ ID NO. 17) |
| | | DNJA3Alu-R | AGGCTGGTAGTGACCTGT GG (SEQ ID NO. 18) |
| HOXB1b | 17 | HOXB1b-F | TCACCCCCATTGCATCTA TT (SEQ ID NO. 19) |
| | | HOXB1b-R | TAGGAAGGGGGTAGGGAG TG(-biotin) (SEQ ID NO. 20) |

TABLE 2-continued

Probes and primers used in this study

| Probe | Chromo-some | Primer Name | Sequence (5'->3') |
|---|---|---|---|
| HOXB1AluL1 | 17 | HOXB1AluL1-F | TCACCCCCATTGCATCTATT (SEQ ID NO. 21) |
| | | HOXB1AluL1-R | TCCCAAAGTGCTAGGATTGC (SEQ ID NO. 22) |
| C1QTNF7 | 4 | C1QTNF7-F | TGCAATTCAAAACAGATTGAAAAT (SEQ ID NO. 23) |
| | | C1QTNF7-R | CCACCATGTGAGAAGTTTGACTAC-biotin (SEQ ID NO. 24) |
| C1QTNF7LTR | 4 | C1QTNF7LTR-F | AAGTGTGAAAGGCATATTTTAGCC (SEQ ID NO. 25) |
| | | C1QTNF7LTR-R | TACATTTTGGGGTCATTTGTTATG (SEQ ID NO. 26) |

Fluorescence in situ Hybridization (FISH)

The method of the present invention can also be utilized in fluorescent in situ hybridization (FISH) experiments. The target region for a FISH probe may be an entire chromosome or only portions thereof. After probe synthesis and labeling[15, 16], FISH hybridization probes can be incubated with synthetic repetitive DNA for repeat suppression instead of Cot-1 DNA prior to hybridization to chromosomes fixed on slides. Often comparative experiments prepared with and without probe prehybridization using Cot-1 DNA show differing probe hybridization signals[14] FISH without Cot-1 DNA probe prehybridization reveals a weaker probe signal on the chromosome as compared to the FISH experiment without Cot-1 DNA prehybridization[14]. The weaker signal stems from hybridization of single copy sequences in the probe to single copy sequences present in the Cot-1 DNA. This reduces the amount of probe available for hybridization to the target sequence on the chromosomes and thus a weaker signal. However, as a consequence, the experiment without Cot-1 DNA prehybridization while brighter in probe signal intensity, typically shows more false positive prove hybridizations, which results in a higher background level making analysis more labor intensive. By prehybridizing probes with a pure synthetic repetitive DNA fraction comprised of no single copy sequences, any repetitive sequences found in the probe are effectively suppressed leaving the single copy sequences available for hybridization to the chromosomes. Thus, probe signal intensity on the chromosome is not comprised and background (false positive hybridization signals) is effectively minimized.

Results

Quantitative Microsphere Hybridization with $C_o t$-1 DNA

A FISH-validated, mixed sc and repetitive sequence probe, ABL1a, from the 5' end of IVS1b of the ABL1 gene containing divergent AluJo/Sx/L2 repeats (chr9:130623551-130625854) was hybridized with biotin-labeled genomic DNA[13, 20]. Although it was expected that commercially prepared $C_o t$-1 DNA would suppress repetitive sequence hybridization, in replicate hybridizations of ABL1a with biotin-labeled genomic DNA, the mean fluorescence (or hybridization) intensity of labeled genomic target was consistently and significantly increased by 2.2 fold when $C_o t$-1 was included in replicate hybridizations of ABL1a with nick-translated genomic DNA (Table 1: Reactions 1 and 2). Sc probes derived from chromosomes 17 genes. PMP22 (Chr17: 15073475-15073576) and TEKT3 (Chr17: 15149108-15149206), showed smaller but reproducible increases of 1.08 and 1.14 fold in hybridization intensity in the presence of $C_o t$-1 DNA (Table 1: Reactions 3-6). These experiments suggested that the effects due to $C_o t$-1 are related to the composition of repetitive sequences surrounding these sc intervals. A sc probe from HOXB1 (Chr17: 43964237-43964330) consistently exhibited a small decrease in hybridization intensity with addition of $C_o t$-1 DNA (Table 1, Reactions 7-12) with a 0.84-0.92 fold decrease in hybridization intensity for genomic samples tested. The HOXB1 interval is practically devoid of repetitive sequences (UCSC Genome Browser, May 2004). The region circumscribing ABL1a contains highly dense, conserved and abundant interspersed SINE (AluJo, AluSx) and LINE (L2) elements. The TEKT3 and PMP22 intervals contain shorter, less abundant and more divergent classes of repeat elements (MIR, MER, and L2).

The degree to which addition of $C_o t$-1 DNA altered target hybridization to the ABL1a probe was determined by comparing hybridizations of biotin-labeled target DNA (detected with streptavidin-phycoerythrin [SPE] in the FL2 channel), a biotin-labeled negative control target (pUC19 plasmid), and each of these with digoxygenin-labeled $C_o t$-1 DNA (detected by FITC-conjugated anti-digoxygenin in the FL1 channel). The presence of $C_o t$-1 resulted in a 2-fold increase in the mean fluorescence intensity for ABL1a hybridized to biotin-labeled homologous genomic target sequence. However, the amount of labeled $C_o t$-1 sequence bound substantially exceeded that necessary for suppression of repetitive sequences in ABL1a, based on a 50 fold increase in intensity relative to reactions in which $C_o t$-1 sequences were omitted (Table 1: Reactions 13 and 14). $C_o t$-1 binding appears sequence-specific, since hybridization of ABL1a to pUC19 exhibited background level signals ($<10^1$), regardless of whether $C_o t$-1 was present (Table 1, Reaction 15). These findings suggest that homologous sequences in $C_o t$-1 are directly binding to the ABL1a probe. Because the ABL1a sequence presumably represents only a small proportion of the $C_o t$-1 target, it alone cannot account for the increase in observed hybridization.

To determine if the increased signal was related to the quantity of $C_o t$-1 DNA, varying amounts of digoxygenin-labeled $C_o t$-1 DNA added to a fixed quantity (50 ng) of biotin-labeled genomic target were hybridized to ABL1b, which is a mixed sc and repetitive probe. ABL1b contains two divergent AluJo repetitive sequences (chr9:130627353-130628735). By doubling the amount of $C_o t$-1 from 50 to 100 ng in the reaction, probe hybridization to $C_o t$-1 increased by 1.8 fold and to homologous target by 1.3 fold (Table 1: Reactions 16 and 17). Similarly, 150 ng of labeled $C_o t$-1 DNA increased hybridization to ABL1b by 3 fold over 50 ng $C_o t$-1, and by 1.5 fold to target DNA (Table 1: Reactions 17 and 18). Even though the stochiometric addition of $C_o t$-1 DNA dilutes the homologous biotinylated target between 2 and 4 fold, the corresponding hybridization intensity is unexpectedly increased 1.5 fold.

The correlation of $C_o t$-1 concentration with hybridization intensity suggested that this reaction component promoted the formation of duplex structures containing other sequences besides the probe and desired genomic target. To determine the composition of $C_o t$-1 derived sequences bound to probes, products were denatured and recovered after hybridization to ABL1a-coupled microspheres (Table 1, Reactions 19 and 20). These products were used as target sequences in subsequent hybridizations to a non-overlapping sc and repetitive microsphere-conjugated probe, ABL1AluMER1, containing Alu elements (AluJb, AluSq, Charlie1, and AluSx) and MER1 sequences localized 2.3 kg centromeric to ABL1a. Given the genomic location of ABL1AluMER1, it was not expected to be present in the recovered nick-translated genomic products. However, the labeled $C_o$t-1 fraction was found to be the source of the recovered ABL1AluMER1 sequence, based on an 11 fold increase in mean fluorescence intensity in FL1 channel (Table 1: Reactions 21 and 22). Repetitive sequences adjacent to hybridized ABL1a in $C_o$t-1 DNA appear to nucleate hybridization to genomic sequences by forming networks of repetitive and single copy sequence elements (FIG. 3: Panels 1 and 2). This possibility was evaluated by quantitative PCR (QPCR) analysis of sequences present in recovered hybridization products.

Analysis of Hybridized Sequences by Quantitative PCR

The content of sc sequences in $C_o$t-1 that were homologous to our probes was determined by QPCR. Probes and primers used in the study are identified in Table 2. Results of the analysis are shown in Table 3.

TABLE 3

Quantitation of recovered hybridization targets

| Reaction | Template | Primer Set | $C_T$ | ng |
|---|---|---|---|---|
| 1 | genomic DNA (500 ng) | ABL1a | 10.88 | 1.73 |
| 2 | $C_o$t-1 DNA (Manufacturer I) (500 ng) | ABL1a | 7.06 | 4.25 |
| 3 | $C_o$t-1 DNA (Manufacturer R) (500 ng) | ABL1a | 9.86 | 3.02 |
| 4 | genomic DNA | RRP4-1.6a5' | 1.734 | n/a |
| 5 | $C_o$t-1 DNA (Manufacturer I) | RRP4-1.6a5' | 2.22 | n/a |
| 6 | $C_o$t-1 DNA (Manufacturer R) | RRP4-1.6a5' | 1.96 | n/a |
| 7 | genomic DNA | RRP4-1.6a | 2.003 | n/a |
| 8 | $C_o$t-1 DNA (Manufacturer I) | RRP4-1.6a | 2.75 | n/a |
| 9 | $C_o$t-1 DNA (Manufacturer R) | RRP4-1.6a | 6.63 | n/a |
| 10 | genomic DNA | RRP4-1.6a3' | 1.881 | n/a |
| 11 | $C_o$t-1 DNA (Manufacturer I) | RRP4-1.6a3' | 1.93 | n/a |
| 12 | $C_o$t-1 DNA (Manufacturer R) | RRP4-1.6a3' | 4.64 | n/a |
| 13 | Recovered ABL1a | ABL1a | 9.23 | n/a |
| 14 | hybridized to genomic DNA with $C_o$t-1 | ABL1a | 1.36 | n/a |
| 15 | Recovered ABL1a | ABL1AluMER1 | 24.29 | 0.009526 |
| 16 | hybridized to genomic DNA with $C_o$t-1 | ABL1AluMER1 | 18.82 | 1.38 |
| 17 | Recovered ABL1a | DNJA3Alu | n/a | n/a |
| 18 | hybridized to genomic DNA with $C_o$t-1 | DNJA3Alu | 30.26 | 2.053 |

A 100 bp sc segment of ABL1a was amplified from 500 ng samples of $C_o$t-1 DNA and control genomic DNA (Table 2). Based on their respective $C_T$ values, the $C_o$t-1 fractions from Manufacturers I and R exhibited a 14 and 2 fold increase, respectively, in the amount of ABL1a hybridized (or a 2.5 and 1.7 molar increase) relative to its normal genomic composition (Table 3: Reactions 1-3). ABL1a sequences were recovered after hybridization to determine the composition of genomic and $C_o$t-1 derived sequences hybridized to this probe (Table 1: Reactions 21 and 22). ABL1a sequences were increased by 128 fold in a hybridized sample containing both target and $C_o$t-1 DNA (Table 3: Reactions 13 and 14). Recovered sequences identical to ABL1AluMER1 from hybridizations containing $C_o$t-1 were 139 fold more abundant than that found in duplicate reactions lacking $C_o$t-1 (Table 3: Reactions 15 and 16). Repetitive sequences that are closely related to ABL1AluMER1 were also detected in recovered hybridization products. An Alu element with 92% similarity, DNJA3Alu (5' to DNJA3 gene chr16: 4421138-4421200), was found in the hybridization reaction containing $C_o$t-1, but not in the reaction lacking $C_o$t-1, indicating the $C_o$t-1 was the source of this contaminating sequence (Table 3: Reactions 17 and 18). Other sc genomic segments (i.e. from CMT1A, HOXB1 and other ABL1 regions (ABL1c and ABL1d) were not detected in the products recovered from hybridization to the ABL1a probe.

$C_o$t-1 derived sequences hybridized to RRP4-1.6a, a sequence linked to ABL1 (Table 2), containing both homologous sc and repetitive sequences, despite the fact that this single copy probe had been validated by FISH[14]. Moderately and highly abundant MIR, L2, and L1 repeat elements surround this sequence in the genome. QPCR demonstrated higher concentrations of repetitive sequences recovered from upstream (5') and downstream (3') amplicons relative to a short RRP4-1.6a product derived from within the sc interval (Table 3: Reaction 4-12). Comparison of $C_T$ values indicates sc sequences bordering genomic repeats (RRP4-1.6a5' and RRP4-1.6a3') are only 6.8 fold more abundant in genomic DNA than in the $C_o$t-1 fraction for Manufacturer R (and similarly, for Manufacturer 1). As expected, the internal sc RRP4-1.6a sequence is considerably more abundant in genomic DNA than in $C_o$t-1 (24 fold), but nevertheless it can still be detected in $C_o$t-1 (Table 3: Reactions 7-9). Enrichment for SINEs and LINEs during $C_o$t-1 preparation results in accretion of linked 1c or sc sequences which, during hybridization, can potentially anneal to the conjugated probe or to actual sc target sequences in labeled genomic DNA.

Suppression of Cross-Hybridization with Synthetic Repetitive DNA

The hybridization effect of $C_o$t-1 DNA was reversed at three different genomic loci by substituting an excess of purified, synthetic DNA(s) prepared specifically from the repetitive elements adjacent to sc sequences (FIG. 4). A 1.9 kb amplification product was synthesized containing a LTR-like repetitive element and a single copy sequence upstream of C1QTNF7 on chromosome 4. The addition of the purified synthetic LTR-like element, C1QTNF7LTR, had no effect on the self-hybridization of this product to coupled microspheres, whereas the addition of $C_o$t-1 DNA increased the mean fluorescence by 1.2 fold (Table 1: Reactions 23-25). C1QTNF7LTR was used to block hybridization of repetitive sequences nick-translated genomic DNA in the presence and absence of $C_o$t-1 DNA and obtained similar results (Table 1: Reactions 26-28). Hybridization of AluSx and L1 repetitive sequences was suppressed within a ~2.3 kb region on chromosome 17 upstream of the HOXB1 locus (HOXB1b) using a synthetic PCR product, HOXB1AluL1, containing these sequences. Hybridization of the HOXB1b PCR product and corresponding microsphere-coupled probe in the presence of the HOXB1AluL1 effectively blocked repetitive sequence within amplified target, and, in fact, reduced hybridization intensity by 0.3 fold, presumably because of the reduction in target length (Table 1: Reactions 32 and 33). Hybridization of repetitive sequences was also effectively suppressed in comparable genomic hybridizations to ABL1a coupled to microspheres by addition of synthetic Alu and L2 elements from within this target region (Table 1: Reactions 29-31).

Impact of $C_ot$-1 in Microarray Hybridization

The nearly universal inclusion of $C_ot$-1 for repeat sequence suppression in published hybridization studies raises the question of how this reagent affects quantitative measures of expression and/or genomic copy number. The variability in dual-label hybridization intensities was evaluated across a set of replicate target samples hybridized to arrays of cloned probes in expression studies that utilized $C_ot$-1 (source data from the GEO database http://www.ncbi.nlm.nih.gov/projects/geo). Results were analyzed from cDNA probes of genes used in the microspheres hybridization assay (including ABL1a, HOXB1, and TEKT3), then subsequently the hybridization profiles for several gene sequences located in genomic environments distinguished by their repetitive sequence composition, i.e. that were either densely (Table 4, bottom) or sparsely (Table 4, top) populated with repetitive sequences.

Discussion

The above-described analyses have demonstrated that non-repetitive sequences present in $C_ot$-1 DNA can significantly alter the amount of labeled genomic target detected in hybridization reactions with homologous probes. Rather than suppressing cross-hybridization, $C_ot$-1 enhanced hybridization to probes containing repetitive sequences by as much as 3 fold. The results suggest that unlabeled $C_ot$-1 DNA sequences bridge 1c and repetitive sequences in sequence specific probes and complementary target sequences. Repetitive sequences linked to homologous 1c sequences in the $C_ot$-1 fraction can nucleate subsequent hybridization of labeled repetitive sequences in genomic targets. The addition of $C_ot$-1 DNA to probe hybridizations with labeled genomic templates catalyzes the formation of a network of heteroduplexes homologous to the probe and elsewhere in the genome (FIG. 3, example 2). "Partial" duplexes containing both 1c and repetitive sequences (FIG. 3, example 3) are facilitated by the addition of $C_ot$-1 DNA through labeled 1c genomic targets to

TABLE 4

Variation among replicate microarray studies for different genes

| Coordinates (hg17) | Gene | Repetitive element(s) | log ratio range | variance | mean | GDS record |
|---|---|---|---|---|---|---|
| Regions containing single copy sequences | | | | | | |
| chr17: 43964237-43964330 | HOXB1 | N/A | 2.44-2.51 | 0.07 | 2.472 | GDS223/31555 |
| chr17: 15149108-15149206 | TEKT3 | N/A | 0.149-0.207 | 0.03 | 0.172 | GDS226/729 |
| chr6: 31,479,350-31,491,069 | MICA | N/A | 2.91-2.93 | 0.02 | 2.92 | GDS223/40755 |
| chr6: 33,166,877-33,173,425 | HIA-SX-alpha | N/A | 2.5-2.54 | 0.04 | 2.519 | GDS223/34072 |
| chr6: 31,546,991-31,548,163 | MHC Class I 38-1 | N/A | 2.43-2.44 | 0.01 | 2.438 | GDS223/34934 |
| chr6: 31,651,329-31,654,091 | TNFalpha | N/A | 2.58-2.65 | 0.07 | 2.614 | GDS223/35402 |
| chr12: 6,179,924-6,217,679 | CD9 | N/A | 2.96-2.97 | 0.01 | 2.966 | GDS223/39389 |
| Regions containing repetitive sequences | | | | | | |
| chr9: 130623551-130625854 | ABL1 (5' IVS1b) | Alu, L2 | (−)0.53-0.14 | 0.67 | −0.0975 | GDS751/20213 |
| chr19: 61581409-61581526 | N/A | L1 | (−)0.22-1.34 | 1.56 | 0.225 | GDS221/H200016688 |
| chr14: 63636408-63636790 | ZFYVE26 | L1 | (−)0.25-0.53 | 0.78 | 0.0825 | GDS221/H200018057 |
| chr6: 43004902-43014978 | TNRC5 | Alu, MIR, L1, L2, LTR | (−)0.248-0.447 | 0.688 | 0.215 | GDS226/11917 |
| chrX: 129482873-129483034 | N/A | retrotransposon L1 | (−)0.47-.06 | 0.53 | −0.225 | GDS221/H200014041 |
| chr14: 67298146-67298238 | N/A | L1, L2 | (−)0.3-0.13 | 0.43 | −0.13375 | GDS221/H200014930 |
| chr10: 15,119,774-15,314,575 | GAPDH | L2, LTR | 1.51-2.12 | 0.61 | 1.7875 | GDS221/H200007830 |
| chr15: 38,115,535-38,118,631 | SRP14 | Simple Repeat | (−)0.38-0.44 | 0.82 | −0.045 | GDS222/H007542 |

Replicate Cy3/Cy5 intensity ratios are significantly more variable for sequences occurring within repeat-dense genomic intervals relative to probes derived from genomic regions containing fewer, more divergent repetitive sequences. For example, ABL1 was found to exhibit both increased and decreased expression using the same test sample in different replicates (e.g. Database record GDS751/20213 which displays a sample variance of 0.30 and p=0.18, Table 4), analogous to the distortion in hybridization we observed with microsphere conjugated-ABL1a. By contrast, HOXB1 showed little variability in log ratio intensities among replicate expression array studies using the same test sample (GDS223/31555, sample variance=0.001 and p<0.0001), consistent with our results for this locus. This suggests that single copy sequences in $C_ot$-1 hybridize to probes, nucleating the formation of mixed sc and repetitive sequence networks that capture labeled repetitive sequences from target cDNA. In microarray studies, $C_ot$-1 thus distorts the hybridization of cloned probes enriched for interspersed repetitive sequences by forming complex hybridization networks in a manner analogous to what is observed in QMH.

linked repetitive elements (FIG. 3, example 4). Labeled repetitive sequences linked to 1c genomic target DNA sequences can also alter hybridization intensities, but not to the same extent that $C_ot$-1 does, due to its enrichment for both 1c and interspersed repetitive sequences.

Since the advent of microarray and array CGH technologies, many researches have noted concerns about experimental reproducibility[4,5]. Perhaps the largest source of variation in relation to cross-hybridization stems from repetitive sequences[7]. However, many researches believe this issue is addressed by blocking repetitive elements with $C_ot$-1 DNA prior to hybridizing cDNA to an array[6,7]. Dong et al.[19] found "some regions of non-repetitive sequences were sufficiently homologous to repetitive sequences to hybridize to the human $C_ot$-1 DNA fraction" and proposed that this was responsible for skewing hybridization intensities in their microarray results. $C_ot$-1 affects the reproducibility of hybridization assays by promoting the formation of repetitive sequence bridges between probes and unrelated, labeled genomic targets. It also contains 1c and sc sequences that compete with labeled targets for probe sites. A more extensive genome-wide analysis is warranted to identify other genomic regions that are more likely to be susceptible to this source of systematic error.

The repetitive component in $C_o t$-1 DNA is fractionated based on reassociation kinetics rather than being explicitly defined based on sequence composition. Because it is not contaminated with 1c sequences, sequence-defined synthetic repetitive DNA is more effective at blocking cross-hybridization by repetitive sequences in probes to paralogous repetitive genomic targets. Another advantage of a locus-specific synthetic reagent is that repeat families that are underrepresented in the $C_o t$-1 DNA fraction, or not represented, due to divergence of repetitive sequence, can be synthesized, providing a more accurate and comprehensive repertoire of genomic repeat sequences free of sc sequences.

Nevertheless, replacement of $C_o t$-1 with a synthetic repetitive DNA reagent that comprehensively represents all known repetitive elements throughout the genome is probably precluded based on the cost and logistical challenges inherent in its preparation. It may be possible to process $C_o t$-1 further in order to limit the amount of contaminating sc sequences that are present. Reannealed repetitive sequences which comprise the majority of double-stranded DNA in $C_o t$-1 are linked to single stranded sequences, which are themselves comprised of single copy and non-overlapping repetitive components. Treatment of these mixed duplex and single stranded structures with an obligatory processive exonuclease, such as Mung Bean Nuclease or Lambda Exonuclease, will trim single stranded sequences protruding from duplex DNA. These enzymes should not cleave at mismatched nucleotides, which are common among related members of the same repetitive sequence family, within single stranded gapped intervals separated by base paired sequences or at nicks in the duplex. This procedure will digest single stranded repetitive sequences and single copy intervals. This will particularly impact the representation of repetitive elements which commonly show 5' (or 3') genomic truncation, such as is seen in L1 retrotransposons[11]. Loss of these sequences could be mitigated by addition of the corresponding synthetic DNA reagents. It should be noted that this treatment of $C_o t$-1 DNA will not completely eliminate all sc sequences because of the possibility that the sc sequences have reannealed, however formation of such duplexes would not be favored by the kinetics of the reaction.

In light of the above, substitution of a partially or completely synthetic blocking reagent composed of defined repetitive sequences in place of $C_o t$-1 DNA should improve the reproducibility of expression microarray and array comparative genomic hybridization. Thus should ultimately lead to standardization of experimental conditions in these widely-used procedures.

REFERENCES

The following reference materials are hereby incorporated by reference.

1. Oostlander, A., Meijer, G. & Ylstra, B. (2004) Microarray-based comparative genomic hybridization and its applications in human genetics. *Clin. Genet.*, 66, 488-95.
2. Hijum, S. V. et al. (2005) A generally applicable validation scheme for the assessment of factors involved in reproducibility and quality of DNA-microarray data. *BMC Genomics*, 6:77.
3. Bammler, T. et al. (2005) Standardizing global gene expression analysis between laboratories and across platforms. *Nature Methods*, 2:351-6.
4. Sherlock, G. (2005) Of FISH and Chips. *Nature Methods*, 2:329-330.
5. Dobbin, K. et al. (2005) Interlaboratory Comparability Study of Cancer Gene Expression Analysis Using Oligonucleotide Microarrays. *Clinical Cancer Research*, 11:565-72.
6. Li, X., Weikuan, G., Mohan S. and Baylink, D. (2002) DNA Microarrays: Their use and misuse, *Microcirculation*, 9:13-22.
7. Wren, J., Kulkarni, A., Joslin, J., Butow, R. and Garner, H. (2002) Cross-hybridization PCR-spotted microarrays. *IEEE Engineering in Medicine and Biology*, 72-75.
8. Marshall, E. (2004) Getting the noise out of gene arrays. *Science*, 306:630-1.
9. Zakharkin, S., Kim, K., Mehta, T., Chen, L., Barnes, S., Scheirer, K., Parrish, R., Allison, D., and Page, G. (2005) Sources of variation in Affymetrix microarray experiments. *BMC Bioinformatics*, 6:214-225.
10. Britten, R., and Kohne, D. (1968) Repeated sequences in DNA. *Science*, 161:529-540.
11. Rogan, P. K. Pan, J., and Weissman, S. M. (1987) L1 repeat elements in the human epsilon-G gamma globin gene intergenic region: sequence analysis and concerted evolution within this family. *Mol. Biol. Evol.* 4 (4):327-42.
12. Carter, N., Fiegler, H. and Piper, J. (2002) Comparative analysis of comparative genomic hybridization microarray technologies: report of a workshop sponsored by the Wellcome Trust. *Cytometry*, 49:43-8.
13. Newkirk, H., Miralles, M., Rogan, P. and Knoll, J. (2006) Determination of genomic copy number with quantitative microsphere hybridization. *Human Mutation* 27:376-386.
14. Rogan, P., Cazcarro, P. and Knoll, J. (2001) Sequence-based design of single-copy genomic DNA probes for fluorescence in situ hybridization. *Genomic Research*, 11:1086-94.
15. Rogan, P. and Knoll, J. (2003) Sequence-based in situ detection of chromosomal abnormalities at high resolution. *American Journal of Medical Genetics*, 121:245-57.
16. Knoll, J., Rogan P. (2004) Single Copy Genomic Hybridization Probes and Method of Generating Same. U.S. Pat. No. 6,828,097.
17. Knoll, J. and Lichter, P. In situ hybridization to metaphase chromosomes and interphase nuclei. (2005) In Dracopoli N., Haines J., Korf B., Moir D., Morton C., Seidman C., Seidman J., Smith D. (eds): "Current protocols in Human Genetics Volume 1" Unit 4.3, Green-Wiley, New York.
18. Ken, W. (2002) BLAT—the BLAST-like alignment tool *Genome Research*, 12:656-64.
19. Dong, S., et al. (2001) Flexible Use of High-Density Oligonucleotide Arrays for Single-Nucleotide Polymorphism Discovery and Validation. *Genomic Research*, 11:1418-1424.
20. Newkirk H., Knoll J., Rogan P. Quantification of Microsphere Suspension Hybridization and Uses Thereof. application Ser. No. PCT/US2006/032693, filed Aug. 16, 2006.

We claim:

1. A method of suppressing non-specific cross-hybridization between repetitive sequences present in nucleic acid probes and homologous repetitive sequences in target genomic nucleic acid, said method comprising the steps of:
   identifying repetitive sequences in a representative genomic region;
   synthesizing suppressive nucleic acid derived from said identified repetitive sequences, said suppressive nucleic acid substantially comprising said identified repetitive sequences and being substantially devoid of low copy sequences; and
   reacting said suppressive nucleic acid with a target nucleic acid thereby causing repetitive sequences in said suppressive nucleic acid to hybridize to homologous repetitive sequences in said target nucleic acid,
   whereby said repetitive sequences in said target nucleic acid are substantially blocked from hybridization with homologous repetitive sequences in a subsequently reacted nucleic acid probe, thereby suppressing non-specific cross-hybridization between said repetitive sequences in said probe and homologous repetitive sequences in said target nucleic acid.

2. The method of claim 1, wherein said target nucleic acid comprises low copy sequences.

3. The method of claim 1, wherein said suppressive nucleic acid is synthesized to contain a plurality of repetitive sequences selected to correspond to repetitive sequences found adjacent to low copy sequences in one or more representative genomic regions.

4. The method of claim 1, comprising the further step of hybridizing said target nucleic acid with one or more probes containing low copy sequences homologous to low copy sequences in said target.

5. The method of claim 1, wherein said probe is substantially devoid of repetitive sequences.

6. The method of claim 1, comprising the step of labeling said probe with a detectable moiety.

7. The method of claim 6, wherein said moiety is selected from the group consisting of fluorophores, enzymatic conjugates, fluorophore-tagged nucleotides, fluorescently-labeled antibodies bound to antigen-bearing nucleotides, biotin-dUTP, digoxygenin-dUTP, and combinations thereof.

8. The method of claim 1, wherein said suppressive nucleic acid is used to block repetitive sequences in an assay selected from the group consisting of microarray hybridization assays, fluorescence in situ hybridization assays, and microsphere hybridization assays.

9. A method of increasing hybridization specificity between low copy number nucleic acid probes and homologous regions in a target nucleic acid, said method comprising the steps of:
   hybridizing repetitive elements in said target nucleic acid with homologous repetitive elements in a suppressive nucleic acid, said suppressive nucleic acid comprising a plurality of repetitive elements and being substantially devoid of low copy number elements; and
   hybridizing low copy number elements in said target nucleic acid with homologous low copy number elements in one or more of said nucleic acid probes.

10. The method of claim 9, wherein said repetitive elements in said suppressive nucleic acid are selected for having substantial homology to repetitive elements flanking low copy elements in one or more representative genomic regions.

11. The method of claim 10, wherein said flanking repetitive elements are of moderate to high copy number.

12. The method of claim 9, wherein said low copy elements comprise single copy elements.

13. The method of claim 9, wherein said probes are substantially devoid of repetitive elements.

14. A method of suppressing non-specific cross-hybridization between repetitive sequences present in nucleic acid probes and homologous repetitive sequences in target genomic nucleic acid, said method comprising the steps of:

identifying repetitive sequences in a representative genomic region;

selecting suppressive nucleic acid derived from said identified repetitive sequences, wherein said suppressive nucleic acid substantially comprises said identified repetitive sequences and is substantially devoid of low copy sequences; and reacting said suppressive nucleic acid with a target nucleic acid, said suppressive nucleic acid thereby causing repetitive sequences in said suppressive nucleic acid to hybridize to homologous repetitive sequences in said target nucleic acid, whereby said repetitive sequences in said target nucleic acid are substantially blocked from hybridization with homologous repetitive sequences in a subsequently reacted nucleic acid probe, thereby suppressing non-specific cross-hybridization between said repetitive sequences in said probe and homologous repetitive sequences in said target nucleic acid.

* * * * *

SEQUENCE LISTING

<160> NUMBER OF SEQ ID NOS: 26

<210> SEQ ID NO 1
<211> LENGTH: 24
<212> TYPE: DNA
<213> ORGANISM: Homo sapiens

<400> SEQUENCE: 1
gtggcttatg cctgtaattt caca                                    24

<210> SEQ ID NO 2
<211> LENGTH: 24
<212> TYPE: DNA
<213> ORGANISM: Homo sapiens

<400> SEQUENCE: 2
agagacaggg tcttcttatg ttgc                                    24

<210> SEQ ID NO 3
<211> LENGTH: 32
<212> TYPE: DNA
<213> ORGANISM: Homo sapiens

<400> SEQUENCE: 3
atttggaaag attatatcca tctacttaat gc                           32

<210> SEQ ID NO 4
<211> LENGTH: 30
<212> TYPE: DNA
<213> ORGANISM: Homo sapiens

<400> SEQUENCE: 4
acaaacctac ctacgtttca acactctctt                              30

<210> SEQ ID NO 5
<211> LENGTH: 30
<212> TYPE: DNA
<213> ORGANISM: Homo sapiens

<400> SEQUENCE: 5
gctttatgaa ctagctgatt tagtttgctc                              30

<210> SEQ ID NO 6
<211> LENGTH: 32
<212> TYPE: DNA
<213> ORGANISM: Homo sapiens

<400> SEQUENCE: 6
ctcaatctct cttttatctg ttttgtccat tg                           32

<210> SEQ ID NO 7
<211> LENGTH: 31
<212> TYPE: DNA
<213> ORGANISM: Homo sapiens

<400> SEQUENCE: 7
tagttaattt agaaggttta aatcacgaga a                            31

<210> SEQ ID NO 8
<211> LENGTH: 29
<212> TYPE: DNA
<213> ORGANISM: Homo sapiens

```
<400> SEQUENCE: 8 ctaatttta aatgtgtgaa tgcaatttt                                          29

<210> SEQ ID NO 9
<211> LENGTH: 24
<212> TYPE: DNA
<213> ORGANISM: Homo sapiens

<400> SEQUENCE: 9
cagaggaagg aagacgtagt gaac                                              24

<210> SEQ ID NO 10
<211> LENGTH: 20
<212> TYPE: DNA
<213> ORGANISM: Homo sapiens

<400> SEQUENCE: 10
gctgaaccaa gcagacacag                                                   20

<210> SEQ ID NO 11
<211> LENGTH: 22
<212> TYPE: DNA
<213> ORGANISM: Homo sapiens

<400> SEQUENCE: 11
atgggagctt ggataagaga tg                                                22

<210> SEQ ID NO 12
<211> LENGTH: 24
<212> TYPE: DNA
<213> ORGANISM: Homo sapiens

<400> SEQUENCE: 12 ctatacctg aggcgataat gttc                                               24

<210> SEQ ID NO 13
<211> LENGTH: 24
<212> TYPE: DNA
<213> ORGANISM: Homo sapiens

<400> SEQUENCE: 13
agcagatcag acatacaggt ccaa                                              24

<210> SEQ ID NO 14
<211> LENGTH: 22
<212> TYPE: DNA
<213> ORGANISM: Homo sapiens

<400> SEQUENCE: 14
ggccaccgta agttacaaga cc                                                22

<210> SEQ ID NO 15
<211> LENGTH: 25
<212> TYPE: DNA
<213> ORGANISM: Homo sapiens
<220> FEATURE:
<221> NAME/KEY: misc_feature
<222> LOCATION: (1)..(1)
<223> OTHER INFORMATION: 12 carbons and an amine are conjugated at the
      5 prime end

<400> SEQUENCE: 15
cctcttcggg gtagagtttc gctct                                             25
```

<210> SEQ ID NO 16
<211> LENGTH: 25
<212> TYPE: DNA
<213> ORGANISM: Homo sapiens

<400> SEQUENCE: 16
ctcaggccct tgtcacactc ttgaa                                  25

<210> SEQ ID NO 17
<211> LENGTH: 20
<212> TYPE: DNA
<213> ORGANISM: Homo sapiens

<400> SEQUENCE: 17
ctcctgtccg tgttctctgc                                        20

<210> SEQ ID NO 18
<211> LENGTH: 20
<212> TYPE: DNA
<213> ORGANISM: Homo sapiens

<400> SEQUENCE: 18
aggctggtag tgacctgtgg                                        20

<210> SEQ ID NO 19
<211> LENGTH: 20
<212> TYPE: DNA
<213> ORGANISM: Homo sapiens

<400> SEQUENCE: 19
tcacccccat tgcatctatt                                        20

<210> SEQ ID NO 20
<211> LENGTH: 20
<212> TYPE: DNA
<213> ORGANISM: Homo sapiens
<220> FEATURE:
<221> NAME/KEY: misc_feature
<222> LOCATION: (20)..(20)
<223> OTHER INFORMATION: biotin conjugated to the 3 prime end

<400> SEQUENCE: 20
taggaagggg gtagggagtg                                        20

<210> SEQ ID NO 21
<211> LENGTH: 20
<212> TYPE: DNA
<213> ORGANISM: Homo sapiens

<400> SEQUENCE: 21
tcacccccat tgcatctatt                                        20

<210> SEQ ID NO 22
<211> LENGTH: 20
<212> TYPE: DNA
<213> ORGANISM: Homo sapiens

<400> SEQUENCE: 22
tcccaaagtg ctaggattgc                                        20

<210> SEQ ID NO 23
<211> LENGTH: 24
<212> TYPE: DNA
<213> ORGANISM: Homo sapiens

```
-continued

<400> SEQUENCE: 23
tgcaattcaa aacagattga aaat                                              24

<210> SEQ ID NO 24
<211> LENGTH: 24
<212> TYPE: DNA
<213> ORGANISM: Homo sapiens
<220> FEATURE:
<221> NAME/KEY: misc_feature
<222> LOCATION: (24)..(24)
<223> OTHER INFORMATION: bioton conjugated to the 3 prime end

<400> SEQUENCE: 24
ccaccatgtg agaagtttga ctac                                              24

<210> SEQ ID NO 25
<211> LENGTH: 24
<212> TYPE: DNA
<213> ORGANISM: Homo sapiens

<400> SEQUENCE: 25
aagtgtgaaa ggcatatttt agcc                                              24

<210> SEQ ID NO 26
<211> LENGTH: 24
<212> TYPE: DNA
<213> ORGANISM: Homo sapiens

<400> SEQUENCE: 26
tacattttgg ggtcatttgt tatg                                              24
```